United States Patent
Gillespie et al.

(10) Patent No.: US 6,608,085 B1
(45) Date of Patent: *Aug. 19, 2003

(54) 4-QUINOLINEMETHANOL DERIVATIVES AS PURINE RECEPTOR ANTAGONISTS (II)

(75) Inventors: Roger John Gillespie, Wokingham (GB); Joanne Lerpiniere, Wokingham (GB); Paul Richard Giles, Wokingham (GB); David Reginald Adams, Wokingham (GB); Lars Jacob Stray Knutsen, Wokingham (GB); Ian Anthony Cliffe, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/786,472

(22) PCT Filed: Sep. 3, 1999

(86) PCT No.: PCT/GB99/02924
§ 371 (c)(1),
(2), (4) Date: May 9, 2001

(87) PCT Pub. No.: WO00/13682
PCT Pub. Date: Mar. 16, 2000

(30) Foreign Application Priority Data

Sep. 4, 1998 (GB) ............................................... 9819384

(51) Int. Cl.$^7$ ..................... A61K 31/4709; A61K 31/47; A61K 31/5377; A61P 25/16; A61P 25/24
(52) U.S. Cl. ..................... 514/314; 514/311; 514/230.5; 514/235.2; 514/302
(58) Field of Search ................................ 514/314, 311, 514/230.5, 235.2, 302

(56) References Cited

U.S. PATENT DOCUMENTS

| | | | | |
|---|---|---|---|---|
| 5,453,426 A | * | 9/1995 | Jacobson et al. | ............ 514/263 |
| 5,786,360 A | * | 7/1998 | Neely | .......................... 514/263 |
| 6,117,884 A | | 9/2000 | Daeuble et al. | ............. 514/311 |
| 6,197,788 B1 | * | 3/2001 | Fletcher et al. | ............. 514/314 |

FOREIGN PATENT DOCUMENTS

| | | |
|---|---|---|
| EP | 0 467 709 | 1/1992 |
| EP | 0 467 710 | 1/1992 |
| WO | 91/01314 | 2/1991 |
| WO | 98/48784 | 11/1998 |
| WO | 98/54190 | 12/1998 |
| WO | 99/26627 | 6/1999 |

OTHER PUBLICATIONS

Wagstaff AJ et al. Drugs and Aging. (1994) 4 (6), 510–540.*
Roth ME. Journal of Family Practice. (1993) 37(6), 593–607.*
Silvia R. Kopf, et al., "Adenosine and memory storage: effect of $A_1$ and $A_2$ receptor antagonists", *Psychopharmacology*, 146:214–219 (1999), Springer–Verlag, Germany.

W.M.H. Behan, et al., "Enhanced neuronal damage by co–administration of quinolinic acid and free radicals, and protection by adenosine $A_{2A}$ receptor antagonists", *British Journal of Pharmacology*, 135:1435–1442 (2002), Nature Publishing Group, USA.

Patrizia Popoli, et al., "Blockade of Striatal Adenosine $A_{2A}$ Receptor Reduces, through a Presynaptic Mechanism, Quinolinic Acid–Induced Excitotoxicity: Possible Relevance to Neuroprotective Interventions in Neurodegenerative Diseases of the Striatum", *The Journal of Neuroscience*, 22(5):1967–1975 (2002), Society for Neuroscience, USA.

Ken Ikeda, et al., "Neuroprotection by adenosine $A_{2A}$ receptor blockage in experimental models of Parkinson's disease", *Journal of Neurochemistry*, 80:262–270 (2002), International Society for Neurochemistry, USA.

Annita Pintor, et al., "SCH 58261 (an adenosine $A_{2A}$ receptor antagonist) reduces, only at low does, $K^{30}$ –evoked glutamate release in the striatum", *European Journal of Pharmacology*, 421:177–180 (2001). Elsevier Science B.V., UK.

Trevor W. Stone, et al., "Neuroprotection by $A_{2A}$ Receptor Antagonists", *Drug Development Research*, 52:323–330 (2001), Wiley–Liss, Inc., UK.

Ennio Ongini, et al., "Dual Actions of $A_{2A}$ Adenosin Receptor Antagonists on Motor Dysfunction and Neurodegenerative Processes", *Drug Development Research*, 52:379–386 (2001), Wiley–Liss, Inc., UK.

(List continued on next page.)

Primary Examiner—Evelyn Mei Huang
(74) Attorney, Agent, or Firm—Foley & Lardner

(57) ABSTRACT

Use of a compound of formula (I) as defined herein, or a pharmaceutically acceptable salt or prodrug thereof, in the manufacture of a medicament for the treatment or prevention of a disorder in which the blocking of purine receptors, particularly adenosine receptors and more particularly $A_{2a}$ receptors, may be beneficial, such as a movement disorder, for example, Parkinson's Disease or progressive supemuclear palsy, Huntingtons disease, multiple system atrophy, corticobasal degeneration, Wilsons disease, Hallerrorder-Spatz disease, progressive pallidal atrophy, Dopa-responsive dystonia-Parkinsonism, spasticity, Alzheimer's disease or other disorders of the basal ganglia which result in dyskinesias.

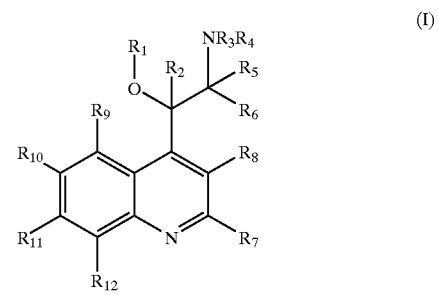

(I)

33 Claims, No Drawings-

OTHER PUBLICATIONS

Angela Monopoli, et al., "Blockade of adenosine $A_{2A}$ receptors by SCH 58261 results in neuroprotective effects in cerebral ischaemia in rats", *NeuroReport*, 9(17): 3955–3959 (1998), Lippincott Williams & Wilkins, USA.

Ongini, E.; Adami, M et al.; Adenosine $A_{2A}$ Receptors and Neuroprotection, Ann. N.Y. Acad. Sci. 825; 30–48; (1997).

Mally & Stone, Potential of Adenosine $A_{2A}$ Receptors . . . CNS Drugs, 10(5), 311–320, (1998).

El Yacoubi et al , Adenosine $A_{2A}$ Receptor Antagonists . . . Br. J. Pharmacol, 134, 68–77 (2001).

Go et al.; Effects of Mefloquine on $Ca^2$ + Uptake by Crude Microsomes of Rabbit Skeletal Muscle; Arch. Int. Pharmacodyn; vol. 329; 1995; pp. 255–271; XP–000889822.

Pinder et al.; "Antimalarials. II. α–(2–Piperidyl)–and α–(2–Pyridyl)–2–trifluoromethyl–4–quinolinemethanols[1b]"; Antimalarials. II; Department of Chemistry, Universtiy of Virginia; Mar. 1968; pp. 267–269; XP–000877337.

Go et al.; "Pharmacological Activity and Structure—Activity Relationship of (±)–erythro–Mefloquine and Related Compounds on the Isolated Mouse Phrenic Nerve Diaphragm Preparation"; Biol. Pharm. Bull.; Pharmaceutical Society of Japan; vol. 16, No. 7; 1993; pp. 668–674; XP–000889819.

Adam; "Nor–Mefloquine: Stereospecific Synthesis and Biological Properties"; Bioorganic & Medical Chemistry Letters; Pergamon Press; vol. 2, No. 1; 1992; pp. 53–58; XP–000889818.

Rainsford; "Effects of Antimalarial Drugs on Interleukin 1–induced Cartilage Proteoglycan degradation in–vitro"; J. Pharm. Pharmacol.; vol. 38; Jun. 11, 1986; pp. 829–833; XP–000889827.

Ngiam et al.; "Stereospecific Inhibition of Cholinesterases by Mefloquine Enantiomers"; Chem. Pharm. Bull.; vol. 35, No. 1; 1987; pp. 409–412; XP–002093900.

Blumbergs et al.; "Antimalarials. 7.2, 8–Bis(trifluoromethyl)–4–quinolinemethanols"; Journal of Medicinal Chemistry; vol. 18, No. 11; 1975; pp. 1122–1126; XP–002110895.

Carroll et al.; "Optical Isomers of Aryl–2–piperidylmethanol Antimalarial Agents, Preparation, Optical Purity, and Absolute Stereochemistry"; Journal of Medicinal Chemistry; vol. 17, No. 2; 1974; pp. 210–219; XP–002093258.

Rosner et al.; "Structure, Chemistry, and Antimalarial Properties of Mefloquine–aziridine"; Heterocycles; vol. 15, No. 2; 1981; pp. 925–933; XP–000889902.

Liu et al.; "Synthesis of 5,6–dihydro–4–hydroxy–2–pyrones Via Formal Cycloaddition Reactions"; Tetrahedron Letters; Pergamon; Elsevier Science Ltd.; pp. 3299–3302.

Maertens et al.; "Inhibition of Volume–Regulated and Calcium–Activated Chloride Channels by the Antimalarial Mefloquine"; The Journal of Pharmacology and Experimental Therapeutics; The American Society for Pharmacology and Experimental Therapeutics; vol. 295, No. 1; 2000; pp. 28–37.

Gribble et al.; "The Antimalarial Agent Mefloquine Inhibits ATP–sensitive K–channels"; British Journal of Pharmacology; Macmillan Publishers Ltd.; vol. 131; 2000; pp. 75–760.

* cited by examiner

4-QUINOLINEMETHANOL DERIVATIVES AS PURINE RECEPTOR ANTAGONISTS (II)

This application is a 371 of PCT/GB99/02924 filed Sep. 3, 1999.

The present invention relates to 4-quinolderivnatives and their use in therapy. In particular, the present invention relates to the treatment of disorders in which the reduction of purinergic neurotransmission could be beneficial. The invention relates in particular to adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Alzheimer's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. el al., *Trends Pharmacol. Sci.* 1997, 18, 338–344) and in the treatment of cerebral ischaemia (Gao, Y. and Phillis, J. W., *Life Sci.* 1994, 55, 61–65). The potential utility of adenosine A2A receptor antagonists in the treatment of movement disorders such as Parkinson's Disease has recently been reviewed (Mally, J. and Stone, T. W., *CNS Drugs*, 1998, 10, 311–320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407–422). This therapeutic potential has resulted in considerable recent research endeavour within the field of adenosine receptor agonists and antagonists (Bhagwhat, S. S.; Williams, M. *Exp. Opin. Ther. Patents* 1995, 5,547–558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143–156). The adenosine receptors are present in the CNS (Fredholm, B. B., *News Physiol. Sci.*, 1995, 10, 122–128).

The design of $P_1$ receptor-mediated agents has been reviewed (Jacobson, K. A., Suzuki, F., *Drug Dev. Res.*, 1997, 39, 289–300; Baraldi, P. G. et al., *Curr. Med. Chem.* 1995, 2, 707–722), and such compounds are claimed to be useful in the treatment of cerebral ischemia or neurodegenerafive disorders, such as Parkinson's disease (Williams, M. and Bumstock, G. *Purinergic Approaches Exp. Ther.* (1997), 3–26. Editor: Jacobson, Kenneth A.; Jarvis, Michael F. Publisher: Wiley-Liss, New York, N.Y.)

The pharmacology of adenosine $A_{2A}$ receptors has been reviewed (Ongini, E.; Fredholm, B. B. *Trends Pharmacol. Sci.* 1996, 17(10), 364–372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Natl. Acad. Sci. U.S.A.* 1991, 88, 7238–41) have been summarised in two more recent articles (Fuxe, K. et al., *Adenosine Adenine Nucleotides Mol. Biol. Integr. Physiol.*, [Proc. Int. Symp.], 5th (1995), 499–507. Editors: Belardinelli, Luiz; Pelleg, Amir. Publisher: Kluwer, Boston, Mass.; Ferre, S. et al., *Trends Neurosci.* 1997, 20, 482–487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 162–4; Mandhane, S. N. et al., *Eur. J. Pharmacol.* 1997, 328, 135–141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder is also treated. The neuroprotective effect of adenosine $A_{2A}$ antagonists has been reviewed (Ongini, E.; Adami, M.; Ferri, C.; Bertorelli, R., *Ann. N. Y. Acad. Sci.* 1997, 825 (Neuroprotective Agents), 30–48).

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett.*, 1993, 323, 141–144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994, 46, 515–517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaninergic function of the nigrostriatal pathway is potentiated by adenosine $A_{2A}$ receptor antagonists (Kanda, T. et al., *Eur. J. Pharmacol.* 1994, 256, 263–268). The structure activity relationship (SAR) of KF 17837 has been published (Shimada, J. et al., *Bioorg. Med. Chem. Lett.* 1997, 7, 2349–2352). Recent data has also been provided on the $A_{2A}$ receptor antagonist KW-6002 (Kuwana, Y et al., *Soc. Neurosci. Abstr.* 1997, 23, 119.14; and Kanda, T. et al., *Ann. Neurol.* 1998, 43(4), 507–513).

New non-xanthine structures sharing these pharmacological properties include SCH 58261 and its derivatives (Baraldi, P. G. et al., Pyrazolo[4,3-e]-1,2,4-triazolo[1,5-c] pyrimidine Derivatives: Potent and Selective $A_{2A}$ Adenosine Antagonists. *J. Med. Chem.* 1996, 39, 1164–71). SCH 58261 (7-(2-phenylethyl)-5-amino-2-(2-furyl)-pyrazolo-[4,3-e]-1, 2,4-triazolo[1,5-c] pyrimidine) is reported as effective in the treatment of movement disorders (Ongini, E. *Drug Dev. Res.* 1997, 42(2), 63–70) and has been followed up by a later series of compounds (Baraldi, P. G. et al., *J. Med. Chem.* 1998, 41(12), 2126–2133).

The foregoing discussion indicates that a potentially effective treatment for movement disorders in humans would comprise agents which act as antagonists at adenosine $A_{2A}$ receptors.

It has now been found that 4-quinolinylmethanol derivatives, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be suitable for the treatment of movement disorders, such as disorders of the basal ganglia which result in dyskinesias. These may include Parkinson's disease, Alzheimer's disease, spasticity, Huntingdon's chorea and Wilson's disease.

According to the present invention there is provided use of a compound of formula (I):

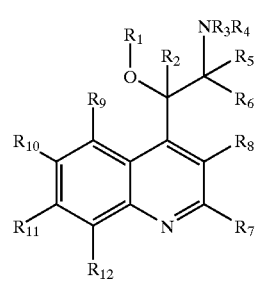

(I)

wherein:

$R_1$ is hydrogen or alkyl;

$R_2$ is selected from hydrogen, alkyl, aryl and 4, 5, 6, 7 or 8 membered saturated and partially unsaturated heterocyclic rings containing one or more heteroatoms selected from O, S and N;

$R_3$ and $R_4$ are independently selected from hydrogen, alky, aryl, $COR_{13}$, $CO_2R_{13}$, $CONR_{13}R_{14}$, $CONR_{13}NR_{14}R_{15}$, $SO_2R_{13}$, $SO_2NR_{13}R_{14}$, $SO_2NR_{13}NR_{14}R_{15}$ and 4, 5, 6, 7 or 8 membered saturated and partially unsaturated heterocyclic rings containing one or more heteroatoms selected from O, S and N, or together may form a 3, 4, 5, 6, 7 or 8 membered saturated, partially unsaturated or aromatic heterocyclic ring optionally containing one or more additional heteroatoms selected from O, S and N;

or $R_1$ and $R_4$ together may form a 5, 6 or 7 membered saturated or partially unsaturated heterocyclic ring optionally containing an additional heteroatom selected from O, S and N;

or $R_2$ and $R_3$ together may form a 4, 5, 6 or 7 membered saturated or partially unsaturated heterocyclic ring optionally containing one or more additional heteroatoms selected from O, S and N;

$R_5$ and $R_6$ are independently selected from hydrogen, alkyl, aryl and 4, 5, 6, 7 or 8 membered saturated and partially unsaturated heterocyclic rings containing one or more heteroatoms selected from O, S and N, or together may form a 3, 4, 5, 6 or 7 membered saturated or partially unsaturated carbocyclic ring or a 4, 5, 6, 7 or 8 membered saturated or partially unsaturated heterocyclic ring containing one or more heteroatoms selected from O, S and N;

or $R_3$ and $R_5$ together may form a 4, 5, 6 or 7 membered unbridged, saturated or partially unsaturated heterocyclic ring optionally containing one or more additional heteroatoms selected from O, S and N;

wherein said carbocyclic or said heterocyclic ring when partially unsaturated or aromatic may be fused to an aryl ring;

with the proviso that where $R_3$ and $R_5$ together form a ring, then $R_3$ and $R_4$ do not also form a ring;

$R_7$, $R_8$, $R_9$, $R_{10}$, $R_{11}$ and $R_{12}$ are independently selected from hydrogen, alkyl, aryl, 4, 5, 6, 7 or 8 membered saturated and partially unsaturated heterocyclic rings containing one or more heteroatoms selected from O, S and N, hydroxy, halogen, nitro, cyano, alkoxy, aryloxy, $COR_{13}$, $OCOR_{13}$, $CO_2R_{13}$, $SR_{13}$, $SOR_{13}$, $SO_2R_{13}$, $SO_2NR_{13}R_{14}$, $CONR_{13}R_{14}$, $CONR_{13}NR_{14}R_{15}$, $OCONR_{13}R_{14}$, $NR_{13}R_{14}$, $NR_{13}COR_{14}$, $NR_{15}CONR_{13}R_{14}$, $NR_{13}CO_2R_{14}$, $NR_{13}SO_2R_{14}$, $CR_{13}NOR_{14}$, $NR_{13}CONR_{14}NR_{15}R_{16}$, $NR_{13}NR_{14}CO_2R_{15}$, $NR_{13}NR_{14}CONR_{15}R_{16}$, $NR_{13}NR_{14}COR_{15}$, $NR_{13}NR_{14}SO_2R_{15}$, $SO_2NR_{13}NR_{14}R_{15}$, $NR_{13}SO_2NR_{14}NR_{15}R_{16}$ and $NR_{13}SO_2NR_{14}R_{15}$, wherein $R_{13}$, $R_{14}$, $R_{15}$ and $R_{16}$ are independently selected from hydrogen, alkyl and aryl, or a pharmaceutically acceptable salt or prodrug thereof, in the manufacture of a medicament for the treatment or prevention of a disorder in which the blocking of purine receptors, particularly adenosine receptors and more particularly $A_{2A}$ receptors, may be beneficial.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, n-propyl, isopropyl n-butyl, isobutyl or t-butyl.

As used herein, the term "aryl" means an aromatic group, such as phenyl or naphthyl, or a heteroaromatic group containing one or more heteroatom, such as pyridyl, pyrrolyl, quinolinyl, furanyl, thienyl, oxadiazolyl, thiadiazolyl, thiazolyl, oxazolyl, isoxazolyl, pryazolyl, triazolyl, imidazolyl or pyrimidinyl.

The alkyl and aryl groups may be substituted or unsubstituted. Where $R_1$ and $R_4$; or $R_2$ and $R_3$; or $R_3$ and $R_4$; or $R_3$ and $R_5$; or $R_5$ and $R_6$ together form a ring, the ring may be substituted or unsubstituted.

Where any group is substituted, there will generally be 1 to 3 substituents present, preferably 1 substituent. Substituents may include: carbon-containing groups such as alkyl, aryl, arylalkyl (e.g. substituted and unsubstituted phenyl, substituted and unsubstituted benzyl);

halogen atoms and halogen-containing groups such as haloalkyl (e.g. trifluoromethyl);

oxygen-containing groups such as alcohols (e.g. hydroxy, hydroxyalkyl, aryl(hydroxy)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy)

and ureas (e.g. mono- or di-alkylaminocarbonylamino or arylaminocarbonylamino);

nitrogen-containing groups such as amines (e.g. amino, mono- or di-alkylamino, aminoalkyl, mono- or di-alkylaminoalkyl), azides, nitriles (e.g. cyano, cyanoalkyl), nitro;

sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);

and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O— and "alkoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical.

As used herein the term "prodrug" means any pharmaceutically acceptable prodrug of the compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are hydrochloric, hydrobromic, phosphoric, sulfuric and methanesulfonic acids, and most particularly preferred is the hydrochloric salt. Acceptable base salts include alkali metal (e.g. sodium, potassium), alkaline earth metal (e.g. calcium, magnesium) and aluminium salts.

As used herein, the term "saturated heterocyclic ring" means a heterocyclic ring wherein the bonds between the atoms forming the ring are single bonds. Examples of such saturated heterocyclic rings include aziridinyl, azetidinyl, pyrrolidinyl, piperidinyl, hexahydroazepinyl, heptamethyleneiminyl, oxiranyl, oxetanyl tetrahydrofuranyl, tetrahydropyranyl, tetrahydrothiophenyl, tetrahydrothiopyran, piperazinyl, morpholinyl, dioxanyl and thiomorpholinyl.

As used herein, the term "partially unsaturated heterocyclic ring" means a heterocyclic ring wherein one or more of the bonds between the atoms forming the ring are unsaturated bonds and wherein the ring is non-aromatic in character. Examples of such partially unsaturated rings include 3-pyrrolinyl, imidazolinyl, oxazolinyl, thiazolinyl, pyrrazolinyl, dihydropyranyl, pyranyl, dihydropyridinyl and tetrahydropyridinyl.

As used herein, the term "carbocyclic ring" means a ring wherein the atoms forming the ring are carbon atoms and wherein the ring is either (a) a saturated ring in which the bonds between the ring atoms are single bonds (such as cyclopropyl, cyclobutyl, cyclopentyl, cyclohexyl, cycloheptyl and cyclooctyl, or a bicyclic ring such as norbomanyl); or (b) a partially unsaturated ring wherein one or more of the bonds between the ring atoms are unsaturated bonds and wherein the ring is non-aromatic in character (such as cyclopentenyl, cyclohexenyl, cycloheptenyl, cyclooctenyl, cyclopentadienyl, cyclohexadienyl and cycloheptadienyl); or (c) an aromatic ring (such as phenyl).

As used herein, the term "unbridged" refers to a ring or ring system which is not bridged; the term "bridged" referring to a ring system in which two or more rings share non-adjacent atoms to form a multicyclic ring system. Examples of a bridged ring system include adamantane, norbomane and 5-ethenyl-1-azabicyclo[2.2.2]octane.

As used herein, the term "fused" refers to a ring system in which two rings or ring systems share only adjacent ring atoms. Examples of a fused ring system include naphthalene, quinoline, indan and benzofuran.

Where any of $R_2$ to $R_{12}$ are selected from 4, 5, 6, 7 or 8 membered heterocyclic rings containing a plurality of heteroatoms selected from O, S and N, the heteroatoms may be the same or different.

Where $R_3$ and $R_4$; or $R_1$ and $R_4$; or $R_2$ and $R_3$; or $R_5$ and R; or $R_3$ and $R_5$ together form a heterocyclic ring containing a plurality of heteroatoms selected from O, S and N, the heteroatoms may be the same or different.

Where $R_3$ and $R_4$ together form a 3 membered heterocyclic ring, it is preferred that said ring is saturated and contains no more than one heteroatom.

In a first embodiment of the invention, $R_1$ is hydrogen or alkyl; $R_2$ is selected from hydrogen, alkyl, aryl and 4, 5, 6, 7 or 8 membered saturated and partially unsaturated heterocyclic rings containing one or more heteroatoms selected from O, S and N; and $R_3$ and $R_4$ are independently selected from hydrogen, alkyl, aryl, $COR_{13}$, $CO_2R_{13}$, $CONR_{13}R_{14}$, $CONR_{13}NR_{14}R_{15}$, $SO_2R_{13}$, $SO_2NR_{13}R_{14}$, $SO_2NR_{13}NR_{14}R_{15}$ and 4,5,6,7 or 8 membered saturated and partially unsaturated heterocyclic rings containing one or more heteroatoms selected from O, S and N, wherein said heterocyclic ring(s) when partially unsaturated may be fused to an aryl ring.

In a second embodiment of the invention, $R_1$ is hydrogen or alkyl; $R_2$ is selected from hydrogen, alkyl, aryl and 4, 5, 6, 7 or 8 membered saturated and partially unsaturated heterocyclic rings containing one or more heteroatoms selected from O, S and N; and $R_3$ and $R_4$ together form a 3, 4, 5, 6, 7 or 8 membered saturated, partially unsaturated or aromatic heterocyclic ring optionally containing one or more additional heteroatoms selected from O, S and N, wherein said heterocyclic ring(s) when partially unsaturated or aromatic may be fused to an aryl ring.

In a third embodiment of the invention, $R_1$ and $R_4$ together form a 5, 6 or 7 membered saturated or partially unsaturated heterocyclic ring optionally containing an additional heteroatom selected from O, S and N; $R_2$ is selected from hydrogen, alkyl, aryl and 4, 5, 6, 7 or 8 membered saturated and partially unsaturated heterocyclic rings containing one or more heteroatoms selected from O, S and N; and $R_3$ is selected from hydrogen, alkyl, aryl, $COR_{13}$, $CO_2R_{13}$, $CONR_{13}R_{14}$, $CONR_{13}NR_{14}R_{15}$, $SO_2R_{13}$, $SO_2NR_{13}R_{14}$, $SO_2NR_{13}NR_{14}R_{15}$ and 4, 5, 6, 7 or 8 membered saturated and partially unsaturated heterocyclic rings containing one or more heteroatoms selected from O, S and N, wherein said heterocyclic ring(s) when partially unsaturated may be fused to an aryl ring.

In a fourth embodiment of the invention, $R_1$ is hydrogen or alkyl; $R_2$ and $R_3$ together form a 4, 5, 6 or 7 membered saturated or partially unsaturated heterocyclic ring optionally containing one or more additional heteroatoms selected from O, S and N; and $R_4$ is selected from hydrogen, alkyl, aryl, $COR_{13}$, $CO_2R_{13}$, $CONR_{13}R_{14}$, $CONR_{13}NR_{14}R_{15}$, $SO_2R_{13}$, $SO_2NR_{13}R_{14}$, $SO_2NR_{13}NR_{14}R_{15}$ and 4, 5, 6, 7 or 8 membered saturated and partially unsaturated heterocyclic rings containing one or more heteroatoms selected from O, S and N, wherein said heterocyclic ring(s) when partially unsaturated may be fused to an aryl ring.

In each of the first, second, third and fourth embodiments set out above, $R_5$ and $R_6$ are independently selected from hydrogen, alkyl (including cycloalkyl, ara-alkyl and heteroara-alkyl), aryl (including heteroaryl) and 4, 5, 6, 7 or 8 membered saturated and partially unsaturated heterocyclic rings containing one or more heteroatoms selected from O, S and N, or together may form a 3, 4, 5, 6 or 7 membered saturated or partially unsaturated carbocyclic ring or a 4, 5, 6, 7 or 8 membered saturated or partially unsaturated heterocyclic ring containing one or more heteroatoms selected from O, S and N, wherein said carbocyclic ring or said heterocyclic ring when partially unsaturated may be fused to an aryl ring.

In a fifth embodiment of the invention, $R_1$ is hydrogen or alkyl; $R_2$ is selected from hydrogen, alkyl, aryl and 4, 5, 6, 7 or 8 membered saturated and partially unsaturated heterocyclic rings containing one or more heteroatoms selected from O, S and N; $R_4$ is selected from hydrogen, alkyl, aryl, $COR_{13}$, $CO_2R_{13}$, $CONR_{13}R_{14}$, $CONR_{13}NR_{14}R_{15}$, $SO_2R_{13}$, $SO_2NR_{13}R_{14}$, $SO_2NR_{13}NR_{14}R_{15}$ and 4, 5, 6, 7 or 8 membered saturated and partially unsaturated heterocyclic rings containing one or more heteroatoms selected from O, S and N; $R_6$ is selected from hydrogen, alkyl, aryl and 4, 5, 6, 7 or 8 membered saturated and partially unsaturated heterocyclic rings containing one or more heteroatoms selected from O, S and N; and $R_3$ and $R_5$ together form a 4, 5, 6 or 7 membered unbridged, saturated or partially unsaturated heterocyclic ring optionally containing one or more additional heteroatoms selected from O, S and N, wherein said heterocyclic ring when partially unsaturated may be fused to an aryl ring.

In each of the first, second, third, fourth and fifth embodiments set out above, $R_7$, $R_8$, $R_9$, $R_{10}$, $R_{11}$ and $R_{12}$ are independently selected from hydrogen, alkyl (including cycloalkyl, halo-alkyl (such as trifluoromethyl), ara-alkyl and heteroara-alkyl), aryl (including heteroaryl), 4, 5, 6, 7 or 8 membered saturated and partially unsaturated heterocyclic rings containing one or more heteroatoms selected from O, S and N, hydroxy, halogen, nitro, cyano, alkoxy, aryloxy, $COR_{13}$, $OCOR_{13}$, $CO_2R_{13}$, $SR_{13}$, $SOR_{13}$, $SO_2R_{13}$, $SO_2NR_{13}R_{14}$, $CONR_{13}R_{14}$, $CONR_{13}NR_{14}R_{15}$, $OCONR_{13}R_{14}$, $NR_{13}R_{14}$, $NR_{13}COR_{14}$, $NR_{15}CONR_{13}R_{14}$, $NR_{13}CO_2R_{14}$, $NR_{13}SO_2R_{14}$, $CR_{13}NOR_{14}$, $NR_{13}CONR_{14}NR_{15}R_{16}$, $NR_{13}NR_{14}CO_2R_{15}$, $NR_{13}NR_{14}CONR_{15}R_{16}$, $NR_{13}NR_{14}COR_{15}$, $NR_{13}NR_{14}SO_2R_{15}$, $SO_2NR_{13}NR_{14}R_{15}$, $NR_{13}SO_2NR_{14}NR_{15}R_{16}$ and $NR_{13}SO_2NR_{14}R_{15}$, wherein $R_{13}$, $R_{14}$, $R_{15}$, and $R_{16}$ are independently selected from hydrogen, alkyl and aryl.

In the compounds of formula (I), where any of $R_2$, $R_3$, $R_4$, $R_5$ and $R_6$ are selected from 4, 5, 6, 7 or 8 membered saturated and partially unsaturated heterocyclic rings containing one or more heteroatoms selected from O, S and N, said heterocyclic ring is preferably unbridged; preferably monocyclic; and is preferably a 5 or 6 membered ring. Where said heterocyclic ring is partially unsaturated and is fused to an aryl ring, said aryl ring is preferably phenyl.

In the compounds of formula (I), where any of $R_7$ to $R_{12}$ are selected from 4, 5, 6, 7 or 8 membered saturated and partially unsaturated heterocyclic rings containing one or more heteroatoms selected from O, S and N, said heterocyclic ring is preferably unbridged; preferably monocyclic; and is preferably a 5 or 6 membered ring.

In the compounds of formula (I), where $R_1$ and $R_4$; or $R_2$ and $R_3$; or $R_3$ and $R_4$; or $R_5$ and $R_6$ together form a ring, said ring is preferably unbridged; preferably monocyclic; and is preferably a 4, 5 or 6 membered ring, preferably a 5 or 6 membered ring. Where any of said rings is partially unsaturated and is fused to an aryl ring, said aryl ring is preferably phenyl.

Preferably, the compounds of formula (I) are selected from compounds in which $R_1$ is hydrogen or methyl or from compounds in which $R_1$ forms a 5 or 6 membered heterocyclic ring with $R_4$.

Preferably, the compounds of formula (I) are selected from compounds in which $R_2$ is hydrogen or from compounds in which $R_2$ forms a 4, 5 or 6 membered, preferably a 4 membered, heterocyclic ring with $R_3$.

$R_3$ and $R_4$ are independently selected from hydrogen, alkyl (including cycloalkyl, ara-alkyl and heteroara-alkyl), aryl (including heteroaryl) $COR_{13}$, $CO_2R_{13}$, $CONR_{13}R_{14}$, $CONR_{13}NR_{14}R_{15}$, $SO_2R_{13}$, $SO_2NR_{13}R_{14}$, $SO_2NR_{13}NR_{14}R_{15}$ and 4, 5, 6, 7 or 8 membered saturated and partially unsaturated heterocyclic rings containing one or more heteroatoms selected from O, S and N, or together may form a 3, 4, 5, 6, 7 or 8 membered saturated, partially unsaturated or aromatic heterocyclic ring optionally containing one or more additional heteroatoms selected from O, S and N, wherein said heterocyclic ring when partially unsaturated or aromatic may be fused to an aryl ring.

Preferably, the compounds of formula (I) are selected from compounds in which $R_3$ is hydrogen, alkyl (preferably methyl, benzyl cyclobutyl or isobutyl), aryl (preferably phenyl), $COR_{13}$ (preferably wherein $R_{13}$ is alllyl, preferably methyl) or $CO_2R_{13}$ (preferably where $R_{13}$ is alkyl, preferably t-butyl), or from compounds in which $R_3$ forms a 5 or 6 membered ring with $R_4$ or from compounds in which $R_3$ forms a 5 or 6 membered heterocyclic ring with $R_5$ or from compounds in which $R_3$ forms a 4, 5 or 6 membered heterocyclic ring with $R_2$.

Preferably, the compounds of formula (I) are selected from compounds in which $R_4$ is hydrogen, alkyl (preferably methyl, cyclobutyl or isobutyl, or ara-alkyl (preferably benzyl or phenylethyl)), aryl (preferably phenyl), $COR_{13}$ (preferably wherein $R_{13}$ is alkyl, preferably methyl) or $CO_2R_{13}$ (preferably where $R_{13}$ is allyl, preferably t-butyl), or from compounds in which $R_4$ forms a 5 or 6 membered heterocyclic ring with $R_3$ or from compounds in which $R_4$ forms a 5 or 6 membered heterocyclic ring with $R_1$.

Preferably, the compounds of formula (I) are selected from compounds in which $R_5$ is hydrogen, alkyl (preferably methyl, secondary butyl or isobutyl or ara-alkyl (preferably benzyl)) or from compounds in which $R_5$ forms a 5 or 6 membered heterocyclic ring with $R_3$.

Preferably, the compounds of formula (I) are selected from compounds in which $R_6$ is hydrogen or alkyl (preferably methyl, secondary butyl or isobutyl or ara-alkyl (preferably benzyl)).

In an embodiment of the invention, where any of $R_4$ to $R_9$ are independently selected from $NR_{13}COR_{14}$, then $R_{13}$ of the or each $NR_{13}COR_{14}$ group is hydrogen.

It is preferred that at least one of $R_7$ to $R_{12}$ is a group other than hydrogen.

In an embodiment of the invention, the compounds of formula (I) are selected from compounds other than compounds in which both $R_7$ and $R_{12}$ are halo-alkyl (including trifluoromethyl). In a further embodiment of the invention, $R_7$ and/or $R_{12}$ are selected from hydrogen, hydroxy, alkyl (preferably unsubstituted alkyl, preferably methyl), alkoxy (preferably methoxy) and $NR_{13}R_{14}$ (preferably where $R_{13}$ and $R_{14}$ are selected from hydrogen and alkyl (preferably methyl)).

In a further embodiment, $R_7$ is selected from hydroxy, $NR_{13}R_{14}$ (preferably where $R_{13}$ and $R_{14}$ are selected from hydrogen and alkyl (preferably methyl), and preferably hydrogen) and alkoxy (preferably methoxy).

In a further embodiment, $R_{12}$ is selected from hydrogen and alkyl (preferably methyl).

Preferably, the compounds of formula (I) are selected from compounds in which $R_8$, $R_9$ $R_{10}$ and/or $R_{11}$ is hydrogen.

In an embodiment of the invention, the compounds of formula (I) are selected from (1R,8aS)-1,5,6,7,8,8a-hexahydro-1-(2,8-bis(trifluoromethyl)-4-quinolinyl)-3H-oxazolo[3,4-a]pyridine, (11R, 2'S)-α-(1-methyl-2-piperidinyl)-2,8-bis(trifluoromethyl)4-quinolinemethanol, (−)-(11R, 2'S)-α-2-piperidinyl-2,8-bis(trifluoromethyl)-4-quinolinemethanol, (−)-(11R, 2'R)-α-2-piperidinyl-2,8-bis(trifluoromethyl)-4-quinolinemethanol and (11S*, 2'R*)-α-(2-Piperidinyl)-2-trifluoromethyl-4-quinolinemethanol.

Where chiral, the compounds of formula (I) may be in the form of a racemic mixture of pairs of enantiomers or in enantiomerically pure form.

Where $R_2$ is H or alkyl, it is preferred that the compounds of formula (I) are selected from compounds in which the stereochemical configuration at the carbon atom bound to the 4-position of the quinoline ring is R.

According to a further aspect of the present invention there is provided a method of treating or preventing a disorder in which the blocking of purine receptors, particularly adenosine receptors and more particularly adenosine $A_{2A}$ receptors, may be beneficial, the method comprising administration to a subject in need of such treatment an effective dose of a compound of formula (I) or a pharmaceutically acceptable salt or prodrug thereof.

The disorder may be caused by the hyperfunctioning of the purine receptors.

According to a further aspect of the present invention there is provided use of a compound of formula (I) or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of formula (I) or a pharmaceutically acceptable salt or prodrug thereof.

According to a further aspect of the invention there is provided use of a compound of formula (I) or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of formula (I) or a pharmaceutically acceptable salt or prodrug thereof.

The medicament for or method of neuroprotection may be of use in the treatment of subjects who are suffering from or at risk from a neurodegenerative disorder, such as a movement disorder.

According to a further aspect of the invention, there is provided for use in therapy a compound of formula (I) wherein $R_1$ and $R_4$ together may form a 5, 6 or 7 saturated, partially unsaturated or aromatic membered heterocyclic ring optionally containing one or more additional heteroatoms selected from O, S and N, or a pharmaceutically acceptable salt or prodrug thereof.

According to a further aspect of the invention there is provided for use in therapy a compound of formula (I) wherein $R_2$ is H or alkyl and wherein the stereochemical configuration at the carbon atom bound to the 4-position of the quinoline ring is R, or a pharmaceutically acceptable salt or prodrug thereof.

The present invention may be employed in respect of a human or animal subject, more preferably a mammal, more preferably a human subject.

The disorders of particular interest are Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the therapy may be of benefit include progressive supernuclear palsy, Huntingtons disease, multiple system atrophy, corticobasal degeneration, Wilsons disease, Hallerrorden-Spatz disease, progressive allidal atrophy, Dopa-responsive dystonia-Parkinsonism, spasticity, Alzheimer's disease or other disorders of the basal ganglia which result in abnormal movement or posture.

A further example of a disorder in which the blocking of purine receptors may be beneficial is depression.

The compound of formula (I) may be used or administered in combination with one or more additional drugs useful in the treatment of movement disorders, such as L-DOPA, the components being in the same formulation or in separate formulations for administration simultaneously or sequentially.

The present invention may also be effective in treating Parkinson's with on-off phenomena; Parkinson's with freezing (end of dose deterioration); and Parkinson's with prominent dyskinesias.

According to a further aspect of the invention, there is provided a compound of formula (I) wherein $R_1$ and $R_4$ together may form a 5, 6 or 7 saturated, partially unsaturated or aromatic membered heterocyclic ring optionally containing one or more additional heteroatoms selected from O, S and N, or a pharmaceutically acceptable salt or prodrug thereof.

According to a further aspect of the invention there is provided a compound of formula (I) wherein $R_2$ is H or alkyl and wherein the stereochemical configuration at the carbon atom bound to the 4-position of the quinoline ring is R, or a pharmaceutically acceptable salt or prodrug thereof.

According to another aspect of the invention there is provided a method of preparing the novel compounds of formula (I). Compounds of formula (I) may be prepared by conventional synthetic methods such as those illustrated in Reaction Schemes 1–5.

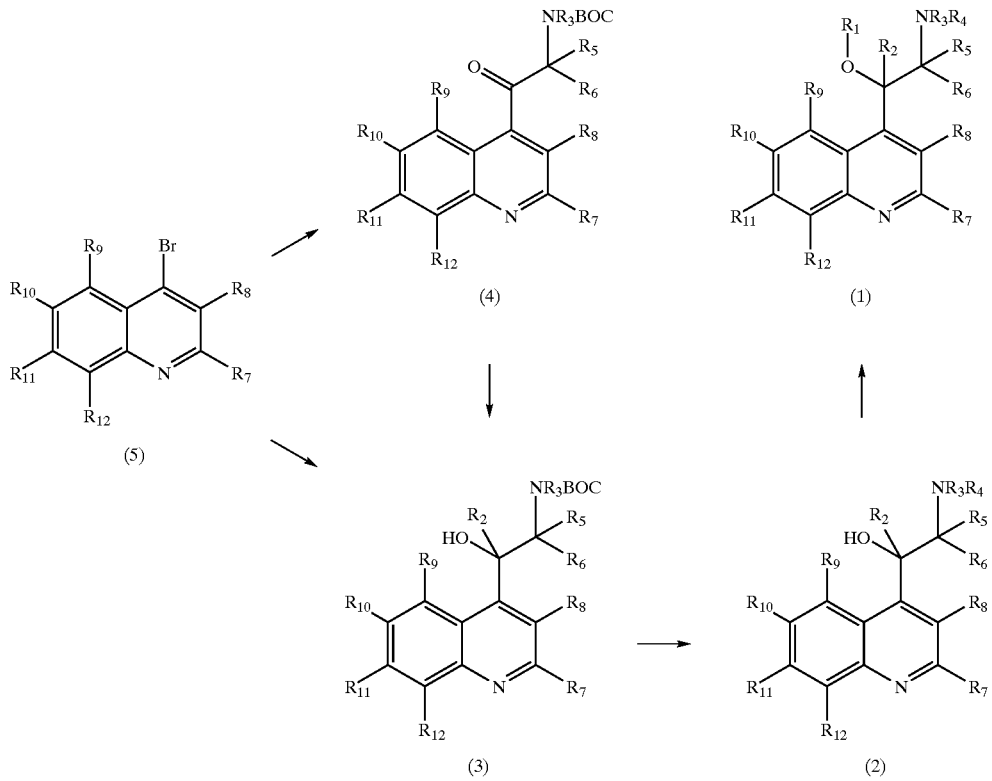

Reaction Scheme 1

Compounds of formula (I) where $R_1$ is an alkyl group are prepared from compounds of formula (2) (Reaction Scheme 1) by standard methods such as alkylation with an alkyl halide in the presence of a suitable base such as NaH.

Compounds of formula (2) where $R_4$ is an alkyl group are prepared from compounds of formula (3) in two steps by standard methods such as removal of the protecting group using, for example TFA, followed by reductive alkylation of the resulting amine using an appropriate aldehyde or ketone in the presence of a suitable reducing agent such as NaCNBH$_3$. Compounds of formula (2) where $R_4$ is hydrogen are prepared from compounds of formula (3) by deprotection as described above.

Compounds of formula (3) where $R_3$ is an alkyl group are prepared from compounds of formula (3) where $R_3$ is hydrogen by standard methods such as alkylation using an appropriate alkyl halide in the presence of a suitable base such as NaH.

Compounds of formula (3) where $R_2$ is hydrogen are prepared from compounds of formula (4) by reaction with a suitable reducing agent such as NaBH$_4$.

Compounds of formula (3) where $R_2$ is an alkyl or aryl group are prepared from compounds of formula (4) by reaction with an appropriate nucleophile such as a Grignard reagent or an alkyl or aryl lithium reagent.

In compounds of formula (4) where $R_5$ and $R_6$ are different, making the carbon to which they are attached a chiral centre, reaction of a nucleophile such as a Grignard reagent, an alkyl or aryl lithium reagent or a hydride reducing agent may lead to compounds of formula (3) where one of the two possible stereochemical configurations at the chiral centre to which $R_2$ is attached, is formed selectively. In favourable cases, such as the addition of hydride reducing agents, it may be possible to selectively prepare compounds of formula (3) with a specific stereochemical configuration at the carbon to which $R_2$ is attached. In such cases suitable hydride reducing agents may be, for example DIBAL which may give a compound of formula (3) with a specific configuration at the carbon to which $R_2$ is attached, or alternatively K-selectride which may give a compound of formula (3) with the opposite configuration at the carbon to which $R_2$ is attached. In such cases the absolute configuration of the carbon to which $R_2$ is attached in the compound of formula (3) will also be determined by the absolute configuration of the carbon to which $R_5$ and $R_6$ are attached. In such cases it may be a possible to selectively synthesise all four of the possible diastereoisomers of a compound of formula (3) where the carbon to which $R_2$ is attached and the carbon to which $R_5$ and $R_6$ are attached are both chiral centres.

Compounds of formula (3) may also be prepared directly from compounds of formula (5), initially by metallation using a suitable metallating agent such as BuLi, followed by addition of a suitably N-protected α-aminoketone or aldehyde such as a compound of formula (19) where $R_2$, $R_3$, $R_5$ and $R_6$ are as defined above.

(19)

In such cases the absolute configuration of the carbon to which $R_2$ is attached in a compound of formula (3) will be determined by the absolute configuration of the carbon to which $R_5$ and $R_6$ are attached in the compound of formula (19). In favourable cases it may be possible to selectively synthesise specific diastereoisomers of a compound of formula (3) by use of an aldehyde or ketone of formula (19) with a specific absolute configuration at the carbon to which $R_5$ and $R_6$ are attached.

Compounds of formula (4) where $R_3$ is alkyl are synthesised by standard methods from compounds of formula (4) where $R_3$ is hydrogen for example by alkylation with a suitable alkyl halide in the presence of a base such as NaH. Compounds of formula (4) are synthesised from compounds of formula (5) by standard methods such as initial metallation by using a suitable metallating agent such as BuLi, followed by addition of a suitably N-protected α-amino acid derivative such as an ester, lactone, acid chloride, acid anhydride, amide or N,O-dialkylhydroxamic acid derivative.

Compounds of formula (I) where $R_3$ or $R_4$ are $COR_{13}$, $CO_2R_{13}$, $CONR_{13}R_{14}$ or $SO_2R_{13}$ may be prepared from compounds of formula (1) where $R_3$ or $R_4$ are hydrogen by standard literature methods such as treatment with an acid chloride ($R_{13}COCl$), chloroformate ($ClCO_2R_{13}$), isocyanate ($R_{13}NCO$), chloroformamide ($ClCONR_{13}R_{14}$) or sulphonyl chloride ($ClSO_2R_{13}$). Compounds of formula (1) where $R_3$ or $R_4$ are $CONR_{13}NR_{14}R_{15}$ may be prepared from compounds of formula (1) where either $R_3$ or $R_4$ are hydrogen by standard literature methods such as treatment with phosgene at low temperature followed by treatment with a suitable substituted hydrazine derivative ($HNR_{13}NR_{14}R_{15}$).

Compounds of formula (2) where $R_3$ and $R_4$ are hydrogen, alkyl or aryl and $R_2$ is hydrogen are synthesised from compounds of formula (6) (Reaction Scheme 2) by reaction with a suitable reducing agent such as $NaBH_4$. Compounds of formula (2) where $R_3$ and $R_4$ are hydrogen, alkyl or aryl and $R_2$ is alkyl or aryl are synthesised from compounds of formula (6) by reaction with a suitable nucleophile such as a Grignard reagent or alkyl or aryl lithium reagent. Compounds of formula (6) where $R_3$ and $R_4$ are hydrogen, alkyl or aryl are synthesised from compounds of formula (7) by standard literature methods such as treatment with a suitably substituted alkyl or aryl amine derivative ($HNR_3R_4$).

Reaction Scheme 2

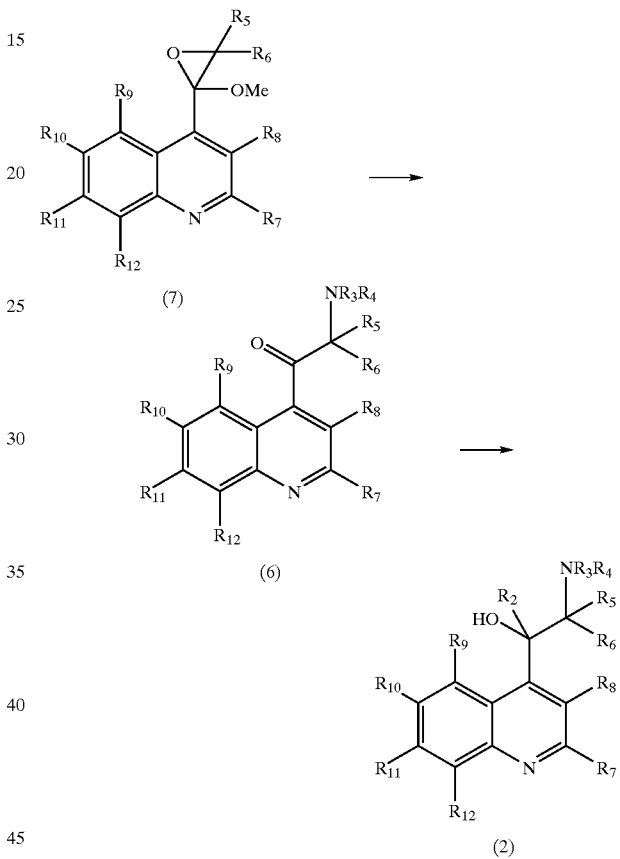

Compounds of formula (8) (Reaction Scheme 3), where n is 1 are synthesised from compounds of formula (2) by standard literature methods such as treatment with phosgene or carbonyl diimidazole. Compounds of formula (8) where n is 0 are synthesised from compounds of formula (2) by standard literature methods such as treatment with formaldehyde.

Compounds of formula (9) are synthesised from compounds of formula (10) by standard literature methods such as reduction with a suitable reducing agent such as borane. Compounds of formula (10) are synthesised from compounds of formula (2) by standard literature methods such as treatment with a suitable α-halo acid halide such as chloroacetyl chloride in the presence of a suitable base such as NaOH. The use of a suitably substituted α-halo acid halide would lead to a compound of formula (11) which is additionally substituted in the azapyran ring.

Compounds of formula (2) where $R_2$, $R_5$ and $R_6$ are hydrogen are synthesised from compounds of formula (11) by standard literature methods such as treatment with a suitably substituted amine ($HNR_3R_4$).

Reaction Scheme 3

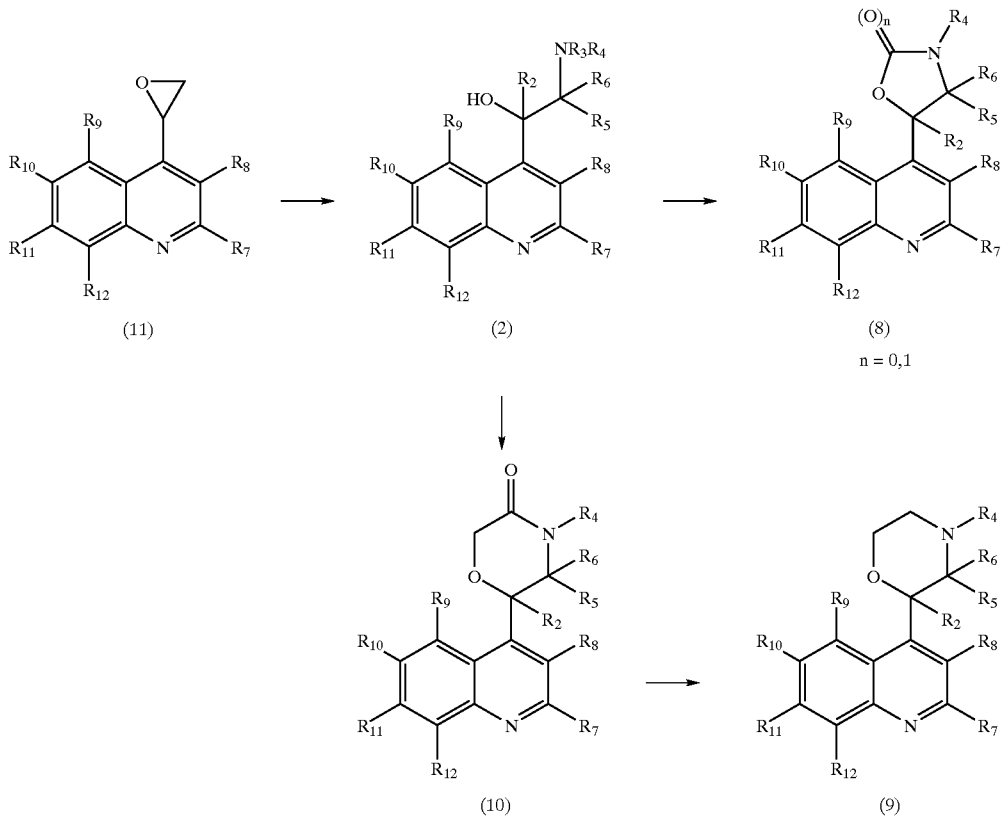

Compounds of formula (2) where $R_3$ and $R_4$ are both hydrogen are prepared from compounds of formula (12) (Reaction Scheme 4) in two steps by standard methods such as initial treatment with a suitable nitro compound ($R_5R_6CHNO_2$) in the presence of a suitable base such as Amberlyst 21, followed by reduction of the intermediate nitro compound with a suitable reducing agent such as zinc in acetic acid.

Reaction Scheme 4

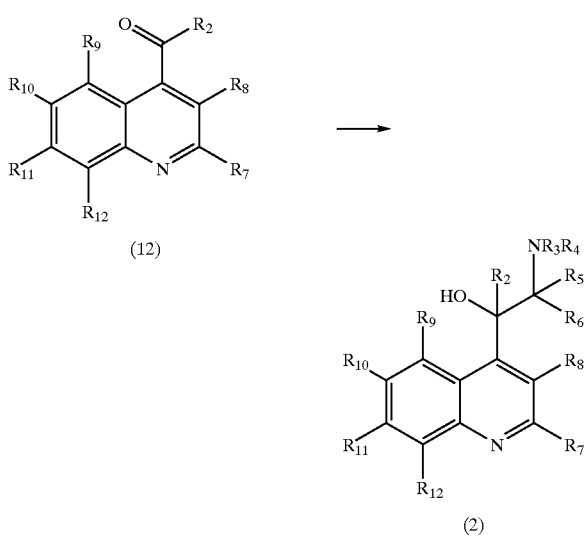

Compounds of formula (7) are known in the literature or are prepared from ketones of formula (14) (Reaction Scheme 5) by standard literature methods such as by α-bromination of the ketone using a suitable brominating agent, followed by treatment with NaOMe. Compounds of formula (14) are known in the literature or are prepared from bromoquinolines of formula (5) by standard literature methods such as by initial metallation with a suitable metallating agent such as BuLi, followed by addition of a suitably activated carboxylic acid derivative such as an ester, lactone, acid chloride, acid anhydride, amide or an N,O-dialkylhydroxamic acid derivative.

Compounds of formula (13), including compounds of formula (11), are known in the literature or are prepared from compounds of formula (14) by standard literature methods such as initial α-bromination using a suitable brominating agent, followed by treatment with a suitable reducing agent such as $NaBH_4$.

Compounds of formula (12) are known in the literature or are synthesised from compounds of formula (5) by standard literature methods such as by initial metallation with a suitable metallating agent such as BuLi, followed by addition of a suitably activated carboxylic acid derivative such as an ester, lactone, acid chloride, acid anhydride, amide or an N,O-dialkylhydroxamic acid derivative.

Compounds of formula (5) are known in the literature or are prepared from compounds of formula (15) by standard methods such as treatment with $POBr_3$. Compounds of formula (5) where $R_7$ is bromine are known in the literature or are prepared directly from anilines of formula (16) by treatment with, for example malonic acid or a suitably substituted malonic acid derivative in the presence of $POBr_3$. 4-Bromoquinolines (5) where $R_7$ is bromine may also be prepared from 4-hydroxyquinolines (15) where $R_7$ is hydroxy, by treatment with POBr₃. 4-Hydroxyquinolines (15) are either known in the literature or are prepared from anilines (16) by standard literature methods such as reaction with a suitably substituted acetoacetate ester derivative in the presence of a suitable acid catalyst or dehydrating agent such as polyphosphoric acid. Anilines (16) are commercially available, are known in the literature or may be prepared by standard literature methods.

The invention further relates to the compounds disclosed herein.

According to a further aspect of the invention, there is provided a pharmaceutical composition comprising a compound of formula (I), or a pharmaceutically acceptable salt or prodrug thereof, in combination with a pharmaceutically acceptable carrier or excipient and a method of making such a composition comprising combining a compound of for-

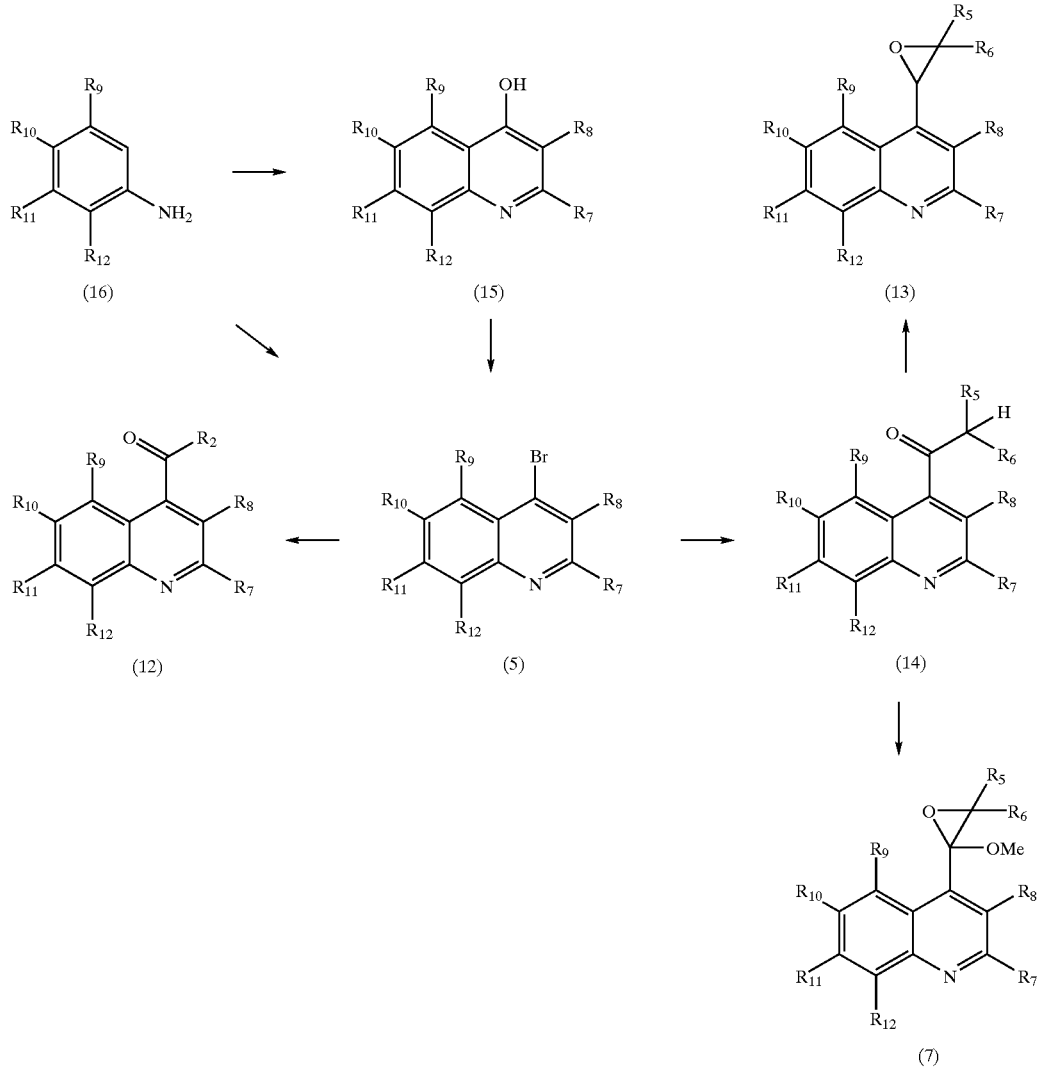

Reaction Scheme 5

Synthetic preparation of some of the compounds of formula (I) where $R_1$–$R_{12}$ are as defined above, may require the use of protecting groups to avoid certain functional groups interfering in the normal course of a reaction. The protecting groups used in the preparation of the compounds of formula (I) are selected from a range of protecting groups commonly used in organic synthesis. This may include, for example the protection of amines with benzyl, substituted benzyl, diphenylmethyl or butoxycarbonyl groups or as a nitro group, the protection of alcohols with, for example benzyl, substituted benzyl, t-butyl or trialkylsilyl groups, and the protection of ketones as ketals or thioketals. In all cases deprotection of these functional groups is carried out by standard literature procedures known to those skilled in the art.

mula (I), or a pharmaceutically acceptable salt or prodrug thereof, with a pharmaceutically acceptable carrier or excipient.

The pharmaceutical compositions employed in the present invention comprise a compound of formula (I), or a pharmaceutically acceptable salt or prodrug thereof, and may also contain other therapeutic ingredients known to those skilled in the art.

Any suitable route of administration may be employed for providing the patient with an effective dosage of a compound of formula (I). For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, the compounds of formula (I), or a pharmaceutically acceptable salt or prodrug thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

EXAMPLES

A number of the compounds of formula (I) are known in the literature and some are widely reported as having antimalarial properties. Assignments of the absolute configurations of derivatives of α-(2-piperidinyl)-2,8-bis(trifluoromethyl)-4-quinolinemethanol have been reported (Carroll, F. I. et al., *J. Med. Chem.* 1974, 17(2), 210–219). However, it is now apparent that the assignments of absolute configurations reported in that publication are erroneous and that the correct assignments are opposite to those reported. For example, (−)-α-2-piperidinyl-2-8-bis(trifluoromethyl)-4-quinolinemethanol is reported in that publication as having the (11S, 2'R) configuration whereas it is now known that the correct configuration for this compound is (11R, 2'S). A number of compounds of formula (I) are synthesised by the methods reported in that publication and are referred to herein using the correct stereochemical assignments in line with current knowledge.

Synthetic Examples

Example 1

(+)-(11S, 2'R)-α-2-Piperidinyl-2,8-bis(trifluoromethyl)-4-quinolinemethanol

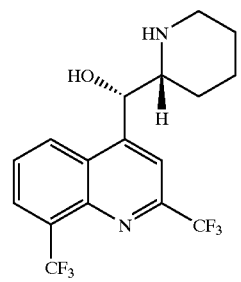

This compound was prepared as reported by Carroll, F. I. et al., (*J. Med. Chem.* 1974, 17(2), 210–219, where the stereochemistry is erroneously reported as (11R, 2'S)).

Example 2

(−)-(11R, 2'S)-α-2-Piperidinyl-2,8-bis(trifluoromethyl)-4-quinolinemethanol

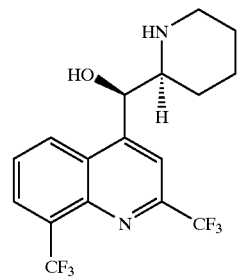

This compound was prepared as reported by Carroll, F. I. et al., (*J. Med. Chem.* 1974, 17(2), 210–219, where the stereochemistry is erroneously reported as (11S, 2'R)).

Example 3

(+)-(11S, 2'S)-α-2-Piperidinyl-2,8-bis(trifluorometbyl)-4-quinolinemethanol

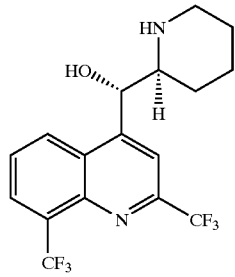

This compound was prepared as reported by Carroll, F. I. et al., (*J. Med. Chem.* 1974, 17(2), 210–219, where the stereochemistry is erroneously reported as (11R, 2'R)).

Example 4

(+)-(11R, 2'R)-α-2-Piperidinyl-2,8-bis(trifluoromethyl)-4-quinolinemethanol

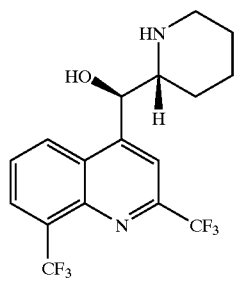

This compound was prepared as reported by Carroll, F. I. et al., (*J. Med. Chem.* 1974, 17(2), 210–219, where the stereochemistry is erroneously reported as (11S, 2'S)).

Example 5

(11R, 2'S)-α-(1-Acetyl-2-piperidinyl)-2,8-bis(trifluoromethyl)-4-quinolinemethanol

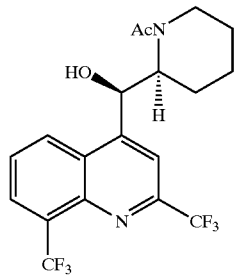

This compound was prepared as reported by Carroll, F. I. et al., (*J. Med. Chem.* 1974, 17(2), 210–219, where the stereochemistry is erroneously reported as (11S, 2'R)).

Example 6

(11S, 2'R)-α-(1-Acetyl-2-piperidinyl)-2,8-bis(trifluoromethyl)-4-quinolinemethanol

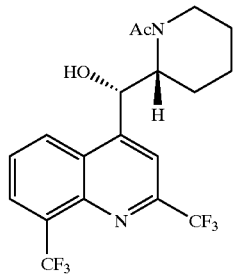

This compound was prepared as reported by Carroll, F. I. et al., (*J. Med. Chem.* 1974, 17(2), 210–219, where the stereochemistry is erroneously reported as (11R, 2'S)).

Example 7

(11R, 2'S)-α-(1-Methyl-2-piperidinyl)-2,8-bis(trifluoromethyl)-4-quinolinemethanol

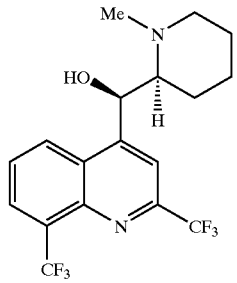

To suspension of (−)-(11R, 2'S)-α-2-Piperidinyl-2,8-bis(trifluoromethyl)-4-quinolinemethanol hydrochloride (0.3 g, 0.72 mmol) in 1,2-dichloroethane (10 mL) was added aqueous formaldehyde (0.6 mL). Sodium triacetoxyborohydride (0.3 g, 1.4 mmol) was added portionwise and the mixture stirred at room temperature for 18 h before water and then aqueous NaHCO$_3$ were added. The mixture was extracted with CH$_2$Cl$_2$ (2×10 mL), the combined extracts washed with aqueous NaHCO$_3$, water and brine, dried (MgSO$_4$) and concentrated in vacuo. A solution of the residue and LiOH (trace) in MEOH (10 mL ) was stirred for 1 h, concentrated in vacuo, and the oily residue purified by chromatography [SiO$_2$; CHCl$_3$—MeOH—NH$_4$OH (100:10:1)] to give the title compound (0.15 g, 53%) as a green-yellow oil: IR $v_{max}$ (Nujol)/cm$^{-1}$ 3405 (b), 2944, 1429,1313, 1188 1140,1108, and 736; NMR $\delta_H$ (400 MHz, CDCl$_3$) 0.52 (1H, d), 0.92 (1H, m), 1.2–1.6 (4H, m), 2.22 (1H, d of t), 2.41 (1H, d of m), 2.61 (3H, s), 3.0 (1H, d), 4.0–4.3 (1H, br s), 5.81 (1H, m), 7.73 (1H, t), 8.10 (2H, m), and 8.16 (1H, s).

The racemic erythro compound has been reported (Biol. Pharm. Bull., 1993, 16, 668)

Example 8

(11R, 2'S)-4-(1-Methoxy-1-(1-methyl-2-piperidinyl)methyl)-2,8-bis(trifluoromethyl)quinoline

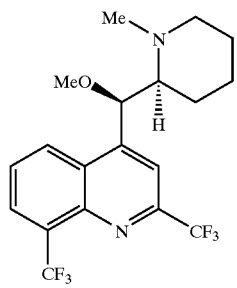

To a solution of (11R, 2'S)-α-(1-methyl-2-piperidinyl)-2,8-bis(trifluoromethyl)-4-quinolinemethanol (80 mg, 0.2 mmol) in THF (5 mL) was added sodium hydride (10 mg, 60% dispersion in oil), the mixture stirred at room temperature for 15 min, iodomethane (3 drops) was added and the mixture stirred for a further 1 h. Water (10 mL) was added, the mixture extracted with $CH_2Cl_2$ (2×10 mL), the combined extracts washed with brine, dried ($MgSO_4$) and concentrated in vacuo. The crude product was purified by chromatography [$SiO_2$; $CHCl_3$—MeOH—$NH_4OH$ (100:10:1)] to give the title compound (35 mg, 42%) as a colourless oil: IR $v_{max}$ (Nujol)/cm$^{-1}$ 2930, 1309, 1191, 1147, 1100 and 735; NMR $\delta_H$ (400 MHz, CDCl$_3$) 0.9–1.7 (6H, m), 2.15 (2H, br m), 2.67 (3H, s), 3.04 (1H, d), 3.40 (3H, s), 5.95 (1H, s), 7.78 (1H, t), 7.88 (1H, s), 8.19 (1H, d), and 8.23 (1H, d).

Example 9

(11R, 2'S)-α-(1-Benzyl-2-piperidinyl)-2,8-bis(trifluoromethyl)-4-quinolinemethanol

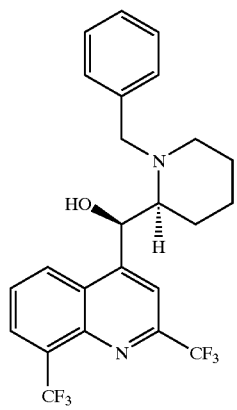

To a solution of (−)-(11R, 2'S)-α-2-piperidinyl-2,8-bis(trifluorometyl)-4-quinolinemethanol hydrochloride (0.265 g, 0.7 mmol) in $CH_2Cl_2$ (10 mL) was added potassium carbonate (0.4 g) in water (10 mL) and the resulting two phase mixture stirred rapidly during dropwise addition of benzyl bromide (0.13 mL, 1.6 mmol). The reaction mixture was stirred for 8 h, the organic phase separated, the aqueous phase re-extracted with $CH_2Cl_2$, and the combined organic phase washed with water (10 mL), brine (10 mL), dried ($MgSO_4$), concentrated in vacuo and the residue purified by chromatography [$SiO_2$, EtOAc-heptane (1:3)] to give the title compound (0.105 g, 32%) as a colourless oil; IR $v_{max}$ (film)/cm$^{-1}$ 3417, 2943, 1602, 1429, 1367, 1309, 1144, 1073, 836, 769, 737, 700, and 664; NMR $\delta_H$ (400 MHz, CDCl$_3$) 0.62 (1H, br d), 0.98 (1H, m), 1.2–1.6 (4H, m), 2.26 (1H, m) 2.85 (1H, d of m), 3.42 (1H, d), 4.4 (1H, br s), 4.58 (1H, d), 6.02 (1H, m), 7.2–7.5 (5H, m), 7.78 (1H, t), 8.08 (1H, d), 8.15 (1H, d), and 8.22 (1H, s).

Example 10

(1R, 8aS)-1,5,6,7,8,8a-Hexahydro-1-(2,8-bis(trifluoromethyl)-4-quinolinyl)-3H-oxazolo[3,4-a]pyridine-3-one

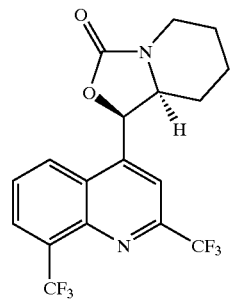

To a suspension of (−)-(11R, 2'S)-α-2-piperidinyl-2,8-bis(trifluoromethyl)-4-quinolinemethanol hydrochloride, (0.21 g, 0.5 mmol) in $CH_2Cl_2$ (20 mL) was added 1,1'-carbonyl diimidazole (0.24 g, 1.5 mmol) and the resulting suspension stirred for 4 h, washed with water (3×10 mL), dried ($MgSO_4$) and concentrated in vacuo. The residue was dissolved in EtOAc and filtered through a pad of silica to give the title compound (0.04 g, 19%) as a white solid: IR $v_{max}$ (Nujol)/cm$^{-1}$ 2924, 1742, 1452, 1313, 1143, and 1114; NMR $\delta_H$ (400 MHz, CDCl$_3$) 0.7–0.9 (2H, m), 1.2–1.8 (8H, m), 3.0 (1H, d of t), 4.05 (1H, d), 4.25 (1H, m), 6.28 (1H, d), 7.80 (1H, t), 7.98 (1H, t), 8.03 (1H, s), and 8.20 (1H, d).

Example 11

(1R, 8aS)-1,5,6,7,8,8a-Hexahydro-1-(2,8-bis(trifluoromethyl)-4-quinolinyl)-3H-oxazolo[3,4-a]pyridine

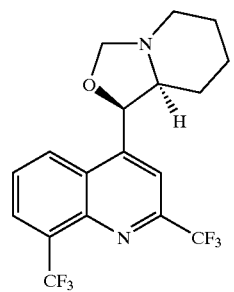

To a solution of (−)-(11R, 2'S)-α-2-Piperidinyl-2,8-bis(trifluoromethyl)-4-quinolinemethanol hydrochloride, (0.5 g, 1.2 mmol) in MeOH (10 mL) was added 5-M NaOH solution then water (30 mL) and the resulting precipitate filtered, washed well with water and air dried. The crude free base was dissolved in MEOH (30 mL), formaldehyde (2 drops, 37% aqueous solution) was added, the mixture refluxed for 3 h, concentrated in vacuo, dissolved in EtOAc and filtered through a pad of $SiO_2$ to give the title compound (0.36 g, 76%) as a pale orange oil: IR $v_{max}$ (Nujol)/cm$^{-1}$ 2924, 1463, 1309, 1186, 1139, and 1111; NMR δ$_H$ (400 MHz, CDCl$_3$) 0.35 (1H, q), 1.1–1.5 (3H, m), 1.52 (2H, m), 2.12 (1H, t), 2.72 (1H, br s), 3.10 (1H, d), 4.05 (1H, br s), 4.90 (1H, s), 5.94 (1H, d), 7.70 (1H, t), 7.99 (1H, s), and 8.1–8.25 (2H, m).

Example 12

(1S*, 8aS*)-1,5,6,7,8,8a-Hexahydro-1-(2,8-bis (trifluoromethyl)-4-quinolinyl)-3H-oxazolo[3,4-a] pyridine-3-one (Racemic)

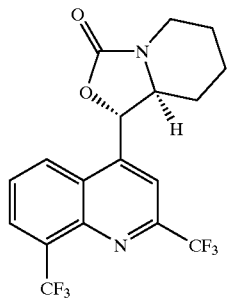

This was prepared by the same method as example 10 using racemic threo α-2-piperidinyl-2,8-bis (trifluoromethyl)-4-quinolinemethanol in place of the (−)-(11R, 2'S) enantiomer and the title compound isolated as a white solid: IR ν$_{max}$ (Nujol)/cm$^{-1}$ 2924, 1760, 1311, 1186, 1140, and 1110; NMR δH (400 MHz, CDCl$_3$) 1.25–1.8 (4H, m), 2.01 (1H, d of m), 2.15 (1H, d of m), 2.81 (1H, d of t), 3.50 (1H, m), 3.95 (1H, d of m), 5.80 (1H, d), 7.80 (1H, t), 7.95 (1H, s), 8.05 (1H, d), and 8.20 (1H, d).

Example 13

(1R, 8aR)-1,5,6,7,8,8a-Hexahydro-1-(2,8-bis (trifluoromethyl)-4-quinolinyl)-3H-oxazolo[3,4-a] pyridine

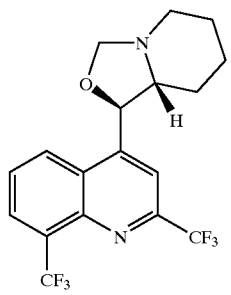

This was prepared by the method of example 11 using (+)-(11R, 2'R)-α-2-piperidinyl-2,8-bis(trifluoromethyl)-4-quinolinemethanol hydrochloride in place of the (−)-(11S, 2'R) enantiomer and the title compound (26 mg, 41%) isolated as a brown oil: IR ν$_{max}$ (Nujol)/cm$^{-1}$ 2942, 1310, 1190, 1147, and 1111; NMR δ$_H$ (400 MHz, CDCl$_3$) 1.2–1.9 (6H, m), 2.45 (2H, m), 3.05 (1H, m), 4.49 (1H, m), 4.89 (1H, m), 5.52 (1H, d), 7,72 (1H, t), 7.98 (1H, s), 8.18 (1H, t), and 8.22 (1H, t).

Example 14

(1R, 9aS)-1,3,4,6,7,8,9,9a-Octahydro-1-(2,8-bis (trifluoromethyl)-4-quinolinyl)-pyrido[2,1-c][1,4] oxazine-4-one

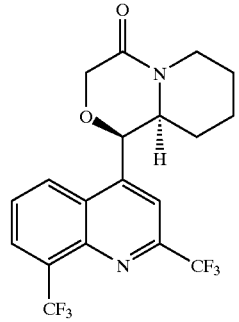

To a suspension of (−)-(11R, 2'S)-α-2-piperidinyl-2,8-bis (trifluoromethyl)-4-quinolinemethanol hydrochloride, (0.5 g, 1.2 mmol) in CH$_2$Cl$_2$ (10 mL) was added a solution of NaOH (0.3 g) in water (5 mL), then chloroacetyl chloride (0.2 g, 1.8 mmol) and the mixture stirred at room temperature for 2 h, diluted with water, the organic phase dried (MgSO$_4$) and concentrated in vacuo. The resulting white solid (0.5 g) was dissolved in 2-propanol (20 mL), KOH (1 pellet) was added, the mixture stirred at room temperature for 2 h, concentrated in vacuo, dissolved in CH$_2$Cl$_2$, washed with water, dried (MgSO$_4$) and concentrated in vacuo. The resulting white solid (0.35 g) was dissolved in EtOAc and filtered through a pad of SiO$_2$ to give the title compound (0.18 g, 35%) as an off-white solid: IR ν$_{max}$ (Nujol)/cm$^{-1}$ 2854, 1653 (b), 1461 (b), 1312, 1136 and 1110; NMR δ$_H$ (400 MHz, CDCl$_3$) 0.72 (1H, s), 1.2–1.7 (6H, m), 1.82 (1H, d), 2.58 (1H, d of t), 3.68 (1H, d), 4.38 (1H, d), 4.52 (1H, d), 4.78 (1, d of m), 5.62 (1H, m), 7.78 (1H, t), 8.02 (1H, s), 8.15 (1H, d), and 8.21 (1H, d).

Example 15

(1R, 9aS)-1,3,4,6,7,8,9,9a-Octahydrol-(2,8-bis (trifluoromethyl)-4-quinolinyl)-pyrido[2,1-c][1,4] oxazine

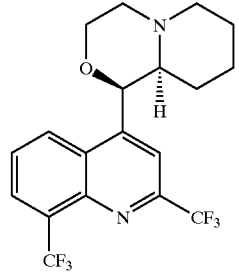

To a solution of (1R, 9aS)-1,3,4,6,7,8,9,9a-octahydro-1-(2,8-bis(trifluoromethyl)-4-quinolinyl)-pyrido[2,1-c][1,4] oxazine-4-one (0.165 g, 0.39 mmol) in anhydrous THF (20 mL) was added borane (0.95 mL, 1-M in THF) and the resulting solution stirred at room temperature for 18 h, treated with acetic acid (1 mL) and stirred for 1 h. The mixture was diluted with aqueous NaOH (10 mL, 2-M), extracted with CH$_2$Cl$_2$ (2×10 mL), the combined extracts washed with brine, dried (MgSO$_4$) and concentrated in vacuo. The resulting colourless oil was dissolved in EtOAc-heptane (1:1), filtered through a pad of SiO₂, concentrated in vacuo, suspended in dilute HCl (5 mL), diluted with THF until homogeneous and stirred at room temperature for 2 days. The mixture was concentrated in vacuo, the residue extracted into CH₂Cl₂, washed with water, dried (MgSO₄) and concentrated in vacuo to give the title compound (37 mg, 23%) as a pale yellow oil: IR $v_{max}$ (Nujol)/cm⁻¹ 2939, 1310, 1277, 1188, 1146 and 1110; NMR $\delta_H$ (400 MHz, CDCl₃) 0.62 (1H, br d), 1.25 (1H, m), 1.7–1.9 (4H, m), 2.42 (1H, m), 2.71 (1H, br t), 3.0–3.1 (2H, m), 3.24 (1H, br t), 3.81 (1H, br t), 4.01 (1H br d), 5.39 (1H, br s), 7.71 (1H, t), 8.15 (1H, d), and 8.2–8.35 (2H, m).

Example 16

(11S, 2'R)-α-2-Pyrrolidinyl-2,8-bis(trifluoromethyl)-4-quinolinemethanol Hydrochloride

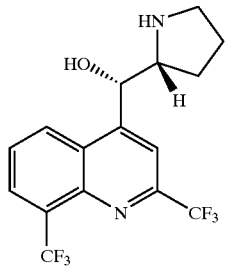

A solution of 4-bromo-2,8-bis(trifluoromethyl)quinoline (0.9 g, 2.6 mmol) in anhydrous ether (30 mL) at −78° C. was treated dropwise with n-butyllithium (1.65 mL, 1.6-M in hexanes, 2.6 mmol) and stirred for 20 min. This solution was then added dropwise via cannula to a solution of (R)-N-tert-butoxycarbonylprolinal (0.4 g, 2.0 mmol) in anhydrous ether (15 mL) at −78° C., the mixture stirred at −78° C. for 1.5 h, then gradually allowed to warm to room temperature. After 19 h, the reaction mixture was concentrated in vacuo and the residue purified by column chromatography [SiO₂; ethyl acetate-heptane(1:1)] to give an inseparable mixture of 2,8-bis(trifluoromethyl)quinoline and (11S, 2'R)-α-(N-tert-butoxycarbonylpyrrolidin-2-yl)-2,8-bis(trifluoromethyl)-4-quinolinemethanol as a brown oil. This mixture was treated with hydrochloric acid (5 mL, 4-M in dioxane), stirred at room temperature for 19 h, concentrated in vacuo and the residue purified by column chromatography [SiO₂; ethyl acetate-heptane (1:1)] to give the title compound (125 mg, 21%) as a pale solid: mp 241–243° C.; IR $v_{max}$ (liquid film)/cm⁻¹ 3219, 2925, 2854, 2367, 1602, 1586, 1573, 1516, 1485, 1435, 1405, 1377, 1313, 1270, 1190, 1140, 1109, 1048 and 1028; NMR $\delta_H$ (400 MHz, CDCl₃) 1.48–1.55 (1H, m), 1.72–1.81 (1H, m), 1.86–1.99 (2H, m), 3.09–3.31 (2H, m), 3.91 (1H, br s), 6.03 (1H, br s), 6.83 (1H, d, J 4 Hz), 8.00 (1 H, t, J 8 Hz), 8.17 (1H, s), 8.42 (1 H, d, J 7 Hz), 8.86 (1 H, d, J 8 Hz), 8.93 (1H, br s) and 9.77 (1H, br s).

The racemic erythro compound has been reported (Bioorg. Med. Chem. Lett., 1992, 2, 53.)

Example 17

(1S, 7aR)-4-(3-oxo-5,6,7,7a-Tetrahydro-[1H, 3H]-pyrrolo[1,2-c]oxazol-1-yl)-2,8-bis(trifluoromethyl) quinoline

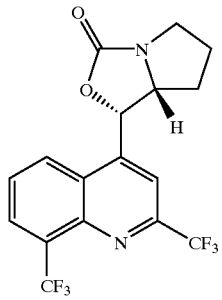

To a solution of (11S, 2'R)-α-2-pyrrolidinyl-2,8-bis (trifluoromethyl)-4-quinolinemethanol hydrochloride (20 mg, 0.05 mmol) in anhydrous CH₂Cl₂ (15 mL) was added triethylamine (8 μL, 0.06 mmol) then carbonyldiimidazole (10 mg, 0.06 mmol) and the mixture stirred for 2 h. The reaction mixture was treated with CH₂Cl₂, washed with water (4×10 mL), dried (MgSO₄) and concentrated in vacuo to afford the desired product (17 mg, 87%) as a pale solid: IR $v_{max}$ (liquid film)/cm⁻¹ 3456, 3086, 2928, 2855, 1761 ,1608, 1589, 1518, 1478, 1462, 1432, 1390, 1307, 1274, 1248, 1272, 1194, 1153, 1109, 1092 and 1061; NMR $\delta_H$ (400 MHz, CDCl₃) 0.84–0.95 (1H, m), 1.16–1.38 (1H, m), 1.81–1.89 (1H, m), 1.96–2.05 (1H, m), 3.29–3.35 (1H, m), 3.72–3.79 (1H, m), 4.51–4.57 (1H, m), 6.44 (1H, d, J 8 Hz), 7.83 (1H, t, J 8 Hz), 8.02 (1H, d, J 8 Hz), 8.07 (1H, s) and 8.25 (1H, d, J 7 Hz).

Example 18

α-Morpholinomethyl-2,8-bis(trifluoromethyl)-4-quinolinemethanol

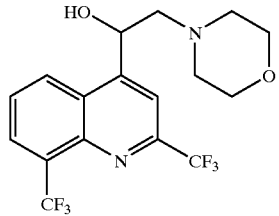

To a solution of 1-(2,8-bis(trifluoromethyl)-4-quinolyl) oxirane (152 mg, 0.5 mmol) in EtOH (1 mL) was added morpholine (131 μL, 1.5 mmol) and the reaction mixture refluxed for 3 h, concentrated in vacuo and purified by chromatography [SiO₂, EtOAc-heptane (2:1)] to give a cream solid. Recrystallisation from EtOAc/heptane gave the title compound (147 mg, 75%) as a white solid: mp 129–130° C.; IR $v_{max}$ (Nujol)/cm⁻¹ 3500–3250, 2954, 2924, 2854, 1603, 1585, 1459, 1310, 1195, 1156 and 1119; NMR $\delta_H$ (400 M, CDCl₃) 2.43–2.63 (3H, m), 2.84–2.88 (3H, m), 3.73–3.88 (4H, m), 4.22–4.45 (1H, br s), 5.61 (1H, d, J 10.1 Hz), 7.73 (1H, dd, J 7.5, 7.9 Hz) and 8.14–8.20 (3H, m); Anal. Calcd for C₁₇H₁₆F₆N₂O₂: C, 51.78; H, 4.09; N, 7.10. Found C, 51.74; H, 4.08; N, 6.96.

Example 19

α-Dimethylaminomethyl-2,8-bis(trifluoromethyl)-4-quinolinemethanol

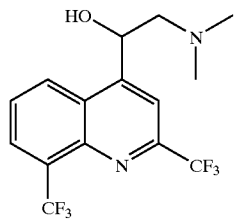

This was prepared from 1-(2,8-bis(trifluoromethyl)-4-quinolyl)oxirane by the method of example 18 using dimethylamine (40% in water) in place of morpholine to give, after recrystallisation (heptane), the title compound (86 mg, 41%) as a cream solid: mp 80.0–80.7° C.; IR $v_{max}$ (Nujol)/cm$^{-1}$ 3510–3300, 2923, 2854, 2785, 1606, 1586, 1517, 1464, 1378, 1308, 1281, 1183, 1166, 1133, 1108 and 768; NMR $\delta_H$ (400 MHz, CDCl$_3$) 2.41–2.51 (7H, m), 2.71 (1H, dd, J 12.6, 2.9 Hz), 4.43–4.54 (1H, br s), 5.52 (1H, dd, J 10.7, 3.1 Hz), 7.72 (1H, t, J 8.0 Hz) and 8.12–8.22 (3H, m);

Example 20

α-Piperidinomethyl-2,8-bis(trifluoromethyl)-4-quinolinemethanol

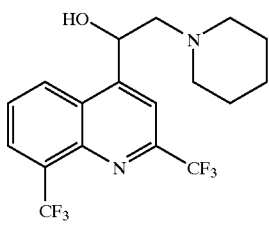

This was prepared from 1-(2,8-bis(trifluoromethyl)-4-quinolyl)oxirane by the method of example 18 using piperidine in place of morpholine to give, after recrystallisation (heptane), the title compound (145 mg, 70%) as a cream solid: mp 129.5° C.; IR $v_{max}$ (Nujol)/cm$^{-1}$ 3295, 2854, 2724, 1606, 1588, 1458, 1428, 1377, 1315, 1192, 1145, 1125 and 1107; NMR $\delta_H$ (400 MHz, CDCl$_3$) 1.47–1.60 (2H, m), 1.60–1.79 (4H, m), 2.36–2.54 (3H, m), 2.73–2.91 (3H, m), 5.53 (1H, dd, J 10.5, 2.9 Hz), 7.71 (1H, t, J 8.1 Hz) and 8.12–8.23 (3H, m); Anal. Calcd for C$_{18}$H$_{18}$F$_6$N$_2$O: C, 55.10; H, 4.62; N, 7.14. Found C, 55.24; H, 4.55; N, 6.93.

Example 21

α-Pyrrolidinomethyl-2,8-bis(trifluoromethyl)-4-quinolinemethanol

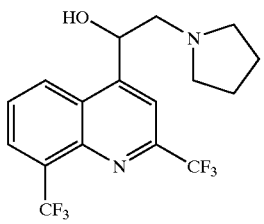

This was prepared from 1-(2,8-bis(trifluoromethyl)-4-quinolyl)oxirane by the method of example 18 using pyrrolidine in place of morpholine to give, after recrystallisation (heptane), the title compound (224 mg, 79%) as a pale solid: mp 92–94° C.; IR $v_{max}$ (Nujol)/cm$^{-1}$ 2925, 2824, 1606, 1506, 1463, 1378, 1309, 1272, 1214, 1194, 1146, 1125 and 1107; NMR $\delta_H$ (400 MHz, CDCl$_3$) 1.86–1.89 (4H, m), 2.64–2.65 (2H, m), 2.75–2.86 (4H, m), 5.51–5.54 (1H, m), 7.72 (1H, t, J 8 Hz) and 8.15–8.24 (3H, m).

Example 22

α-Methylaminomethyl-2,8-bis(trifluoromethyl)-4-quinolinemethanol

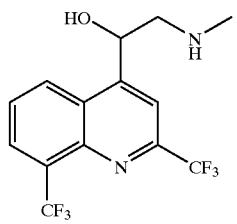

This was prepared from 1-(2,8-bis(trifluoromethyl)-4-quinolyl)oxirane by the method of example 18 using methylamine (40% in water) in place of morpholine to give, after recrystallisation (EtOAc), the title compound (119 mg, 72%) as a white solid: mp 158° C.; IR $v_{max}$ (Nujol)/cm$^{-1}$ 3299, 2924, 2854, 2660, 1600, 1465, 1376, 1309, 1296, 1183, 1165, 1136 and 1109; NMR $\delta_H$ (400 MHz, DMSO-d$_6$) 1.74–2.0 (1H, br s), 2.29 (3H, s), 2.75 (1H, dd, J 12.5, 3.8 Hz), 5.60 (1H, dd, J 6.0, 4.5 Hz), 5.91–6.07 (1H, br s), 7.92 (1H, dd, J 8.1, 7.9 Hz), 8.12 (1H, s), 8.35 (1H, d, J 7.6 Hz) and 8.64 (1H, d, J 8.5 Hz); Anal. Calcd for C$_{14}$H$_{21}$F$_6$NO$_2$: C, 49.71; H, 3.58; N, 8.28. Found C, 49.39; H, 3.51; N, 7.99.

Example 23

α-Phenylaminomethyl-2,8-bis(trifluoromethyl)-4-quinolinemethanol

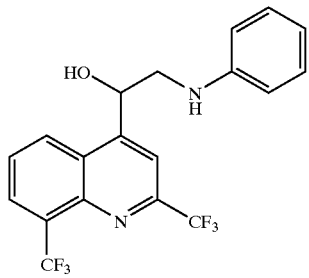

This was prepared from 1-(2,8-bis(trifluoromethyl)-4-quinolyl)oxirane by the method of example 18 using aniline in place of morpholine to give, after recrystallisation (CH$_2$Cl$_2$-heptane), the title compound (145 mg, 80%) as a cream solid: mp 121.1–121.6° C.; IR $v_{max}$ (Nujol)/cm$^{-1}$ 3319, 3164, 2924, 2854, 1604, 1496, 1462, 1377, 1310, 1107, 1085 and 765; NMR $\delta_H$ (400 MHz, CDCl$_3$) 2.91 (1H, d, J 3.7 Hz), 3.35 (1H, dd, J 12.9, 9.5 Hz), 3.69 (1H, d, J 13.5 Hz), 4.09–4.18 (1H, br s), 5.71–5.78 (1H, m), 6.73 (2H, d, J 13.5 Hz), 6.83 (1H, t, J 7.2 Hz), 7.20–7.28 (2H, m), 7.76 (1H, dd, J 7.2, 8.4 Hz), 8.14 (1H, s), 8.20 (1H, d, J 7.1 Hz) and 8.30 (1H, d, J 8.5 Hz).

Example 24

α-Benzylaminomethyl-2,8-bis(trifluoromethyl)-4-quinolinemethanol

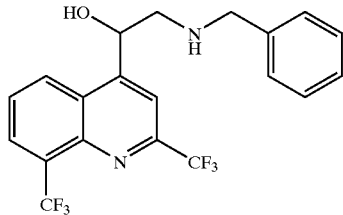

This was prepared from 1-(2,8-bis(trifluoromethyl)-4-quinolyl)oxirane by the method of example 18 using benzylamine in place of morpholine and the title compound (171 mg, 69%) was isolated as a cream solid: mp 138.1–138.6° C.; IR $v_{max}$ (Nujol)/cm$^{-1}$ 3289, 2925, 2854, 2710, 1604, 1586, 1455, 1376, 1319, 1216, 1181, 1163, 1133, 1108, 770 and 698; NMR $\delta_H$ (400 MHz, CDCl$_3$) 2.76 (1H, dd, J 9.0, 12.5 Hz), 3.18 (1H, dd, J 12.5, 3.5 Hz), 3.87 (1H, d, J 13.2 Hz), 3.92 (1H, d, J 13.2 Hz), 5.44 (1H, dd, J 9.0, 3.5 Hz), 7.19–7.36 (5H, m), 7.67 (1H, t, J 7.8 Hz) and 8.02–8.15 (3H, m); Anal. Calcd for C$_{20}$H$_{16}$F$_6$N$_2$O: C, 57.98; H, 3.89; N, 6.76. Found C, 57.89; H, 3.92; N, 6.67.

Example 25

α-Isobutylaminomethyl-2,8-bis(trifluoromethyl)-4-quinolinemethanol

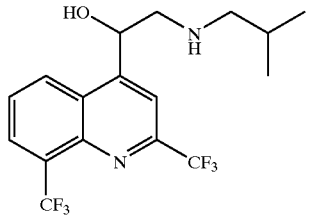

This was prepared from 1-(2,8-bis(trifluoromethyl)-4-quinolyl)oxirane by the method of example 18 using isopropylamine in place of morpholine and the title compound (203 mg, 89%) was isolated as a cream solid: mp 132.1–132.4° C.; IR $v_{max}$ (Nujol)/cm$^{-1}$ 3318, 2924, 2854, 2725, 1604, 1586, 1465, 1429, 1377, 1319, 1189, 1138, 1106 and 770; NMR $\delta_H$ (400 Hz, CDCl$_3$) 0.95 (6H, d, J 5.5 Hz), 1.71–1.81 (1H, m), 2.48 (1H, dd, J 11.6, 6.5 Hz), 2.56 (1H, dd, J 11.6, 6.9 Hz), 2.69 (1H, dd, J 12.2, 9.0 Hz), 3.18 (1H, dd, J 12.2, 3.8 Hz), 5.46 (1H, dd, J 9.0, 3.8 Hz), 7.72 (1H, t, J 7.9 Hz), 8.13 (1H, s), 8.22 (1H, d, J 8.5 Hz) and 8.16 (1H, d, 7.1 Hz).

Example 26

α-Cyclobutylaminomethyl-2,8-bis(trifluoromethyl)-4-quinolinemethanol

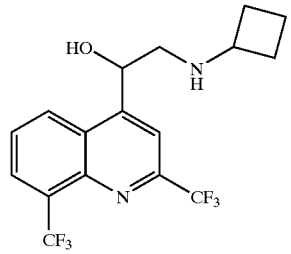

This was prepared from 1-(2,8-bis(trifluoromethyl)-4uinolyl)oxirane by the method of example 18 using cyclobutylamine in place of morpholine and the title compound (117 mg, 54%) isolated as a cream solid: mp 144.6–145.2° C.; IR $v_{max}$ (Nujol)/cm$^{-1}$ 3277, 2924, 2854, 2727, 1604, 1586, 1513, 1456, 1426, 1376, 1319, 1309, 1157, 1131, 1104,945, 895 and 768; NMR $\delta_H$ (400 MHz, CDCl$_3$) 1.62–1.82 (4H, m), 2.18–2.30 (2H, m), 2.63 (1H, dd, J 12.6, 8.5 Hz), 3.11 (1H, dd, J 12.6, 3.9 Hz), 3.28–3.38 (1H, m), 5.44 (1H, dd, J 8.5, 3.9 Hz), 7.72 (1H, t, J 7.9 Hz), 8.11 (1H, s), 8.16 (1H, d, J 6.8 Hz) and 8.19 (1H, d, J 8.7 Hz); Anal. Calcd for C$_{17}$H$_{16}$F$_6$N$_2$O: C, 53.97; H, 4.26; N, 7.40. Found C, 53.92; H, 4.26; N, 7.23.

Example 27

4-(3-Benzyl-2,3,4,5-tetrahydro-5-oxazolyl)-2,8-bis(trifluoromethyl)quinoline

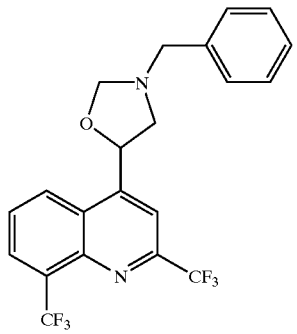

To a solution of α-benzylaminomethyl-2,8-bis(trifluoromethyl)-4-quinolinemethanol (142 mg, 0.34 mmol) in MeOH (3 mL) was added formaldehyde (0.2 mL, 37% in water), the mixture was refluxed for 30 mins, cooled, concentrated in vacuo, and the residue was suspended in heptane and filtered to give the title compound (41 mg, 28%) as a white solid: mp 108.5–108.9° C.; IR $v_{max}$ (Nujol)/cm$^{-1}$ 2924, 2854, 1602, 1586, 1458, 1378, 1306, 1271, 1184, 1153, 1139, 1127, 1105, 775 and 726; NMR $\delta_H$ (400 MHz, CDCl$_3$) 2.85 (1H, dd, J 11.7, 7.0 Hz), 3.77 (1H, dd, J 11.7, 7.4 Hz), 3.85 (1H, d, J 13.1 Hz), 3.90 (1H, d, 13.1 Hz), 4.71 (1H, d, J 5.8 Hz), 4.74 (1H, d, J 5.8 Hz), 5.72 (1H, t, J 7.0 Hz), 7.21–7.43 (5H, m), 7.72 (1H, t, J 7.9 Hz), 8.17 (1H, d, J 7.5 Hz), 8.11 (1H, s) and 8.03 (1H, d, J 8.1 Hz).

Example 28

4-(3-Isobutyl-2,3,4,5-tetrahydro-5-oxazolyl)-2,8-bis(trifuoromethyl)quinoline

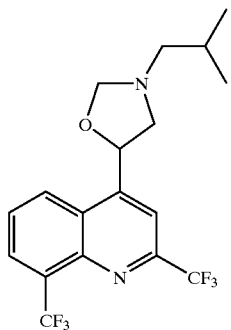

This was prepared from α-isobutylaminomethyl-2,8-bis(trifluoromethyl)-4-quinolinemethanol by the method of example 27 and the title compound (70 mg, 85%) isolated as a pale yellow oil: IR $v_{max}$ (Nujol)/cm$^{-1}$ 2960, 2931, 2875, 1604, 1586, 1430, 1308, 1189, 1145, 1108, 1081 and 769; NMR $\delta_H$ (400 MHz, CDCl$_3$) 0.92 (3H, d, J 6.6 Hz), 0.94 (3H, d, J 6.9 Hz), 1.64–1.72 (1H, m), 2.41 (1H, dd, J 12.0, 6.8 Hz), 2.45 (1H, dd, J 12.0, 7.5 Hz), 2.78 (1H, dd, J 11.1, 7.0 Hz), 3.70 (1H, dd, J 11.1, 7.2 Hz), 4.64–4.67 (2H, m), 5.65 (1H, t, J 7.1 Hz), 7.73 (1H, t, J 7.8 Hz), 8.07 (1H, s), 8.09 (1H, d, J 7.9 Hz) and 8.17 (1H, d, 7.7 Hz);

Example 29

4-(1-Methoxy-2-(1-piperidinyl)ethyl)-2,8-bis(trifluoromethyl)quinoline

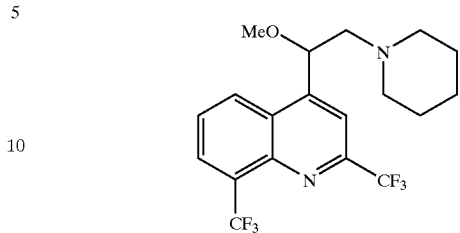

To an ice-cold solution of α-piperidinomethyl-2,8-bis(trifluoromethyl)-4-quinolinemethanol (60 mg, 0.15 mmol) in THF (1.5 mL) was added NaH (6 mg, 60% dispersion in oil, 0.15 mmol), the mixture stirred at 0° C. for 30 min, treated with methyl iodide (10 μL, 0.16 mmol), allowed to warm to room temperature and stirred for 1 h. The reaction mixture was poured into saturated NaHCO$_3$, extracted with EtOAc (2×20 mL), the combined extracts dried (MgSO$_4$), concentrated in vacuo and purified by chromatography [SiO$_2$, EtOAc] to give the title compound (62 mg, 100%) as a pale yellow oil: IR $v_{max}$ (Nujol)/cm$^{-1}$ 2937, 2855, 2824, 1603, 1585, 1309, 1188, 1147, 1108 and 769; NMR $\delta_H$ (400 MHz, CDCl$_3$) 1.40–1.45 (2H, m), 1.52–1.66 (4H, m), 2.44–2.61 (5H, m), 2.84 (1H, dd, J 13.9, 7.8 Hz), 5.14 (1H, dd, J 7.8, 3.3), 7.74 (1H, t, J 7.7 Hz), 7.92 (1H, s), 8.17 (1H, d, J 6.9 Hz) and 8.45 (1H, d, J 8.5 Hz).

Example 30

N-Benzyl-β-methoxy-2,8-bis(trifuoromethyl)-4-quinolineethanamine Hydrochloride

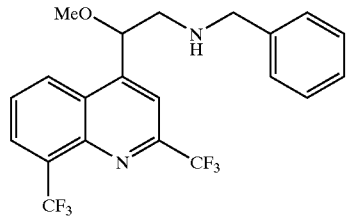

α-(N-Benzyl-tert-butoxyarbonylaminomethyl)-2,8-bis(trifluoromethyl)-4-quinolinemethanol To α-benzylaminomethyl-2,8-bis(trifluoromethyl)-4-quinolinemethanol (100 mg, 0.24 mmol) in dioxan (2 mL) was added di-t-butyl dicarbonate (53 mg, 0.24 mmol) and saturated NaHCO$_3$ (1 mL). The reaction mixture was stirred at room temperature for 30 min, poured into water, extracted with EtOAc (2×10 mL), the extracts dried (MgSO$_4$) and concentrated in vacuo to give the product (123 mg, 100%) as a pale yellow oil: NMR $\delta_H$ (400 MHz, CDCl$_3$) 1.54 (9H, s), 3.54 (2H, s), 4.05 (1H, d, J 15.6 Hz), 4.66 (1H, d, J 15.6 Hz), 5.25 (1H, s), 5.60–5.68 (1H, m), 7.08–7.21 (3H, m), 7.21–4,38 (2H, m), 7.60 (1H, t, J 7.7 Hz), 7.86 (1H, d, J 8.2 Hz) and 8.09–8.12 (2H, m).

N-Benzyl-N-tert-butoxyarbonyl-β-methoxy-2,8-bis(trifluoromethyl)-4-quinolineethanamine To an ice-cold solution of α-(N-benzyl-tert-butoxycarbonylaminomethyl)-2,8-bis(trifluoromethyl)-4-quinolinemethanol (118 mg, 0.23 mmol) in THF (1 mL) was added NaH (9 mg, 60% dispersion in oil, 0.23 mmol) and the mixture stirred at 0° C. for 10 min. Methyl iodide (15 mL, 0.24 mmol) was added, and the mixture allowed to warm to room temperature, stirred for 1 h, poured into saturated NaHCO$_3$ and extracted with EtOAc (2×30 mL). The combined extracts were dried (MgSO$_4$), concentrated in vacuo and purified by chromatography [SiO$_2$, heptane-EtOAc (2:1)] to give the product (118 mg, 97%) as a pale yellow oil: NMR $\delta_H$ (400 MHz, CDCl$_3$) (70:30 mixture of rotamers) 1.40 and 1.49 (9H, 2×s), 3.14 and 3.31–3.39 (1H, dd, J 14.4, 8.9 Hz and m), 3.33 and 3.37 (3H, 2×s), 3.65 and 3.74 (1H, 2×d, J 14.8 Hz), 4.36 and 4.50 (1H, 2×d, J 15.6 Hz), 4.73 and 4.83 (1H, 2×d, J 15.6 Hz), 5.07–5.14 and 5.38–5.42 (1H, 2×m), 7.10–7.18 (2H, m), 7.18–7.34 (3H, m), 7.69 and 7.80 (1H, 2×t, J 7.9 Hz), 7.84 and 7.91 (1H, 2×s), 8.17 (1H, d, J 7.7), 8.39 and 8.74 (1H, 2×d, J 8.2 Hz).

N-Benzyl-β-methoxy-2,8-bis(trifluoromethyl)-4-quinolineethanamine Hydrochloride

To N-Benzyl-N-tert-butoxycarbonyl-β-methoxy-2,8-bis(trifluoromethyl)-4-quinolineethanamine (113 mg, 0.21 mmol) in dioxan (1 mL) was added HCl (4-M in dioxan, 0.25 mL, 1 mmol) and the mixture stirred at room temperature for 1 h. The mixture was concentrated in vacuo, triturated with ether and filtered to give the title compound (54 mg, 60%) as a white solid: mp 232–233° C.; NMR $\delta_H$ (400 MHz, DMSO-d$_6$) 3.17–3.41 (2H, m), 3.34 (3H, s), 4.19 (1H, d, J 13.8 Hz), 4.22 (1H, d, J 13.8 Hz), 5.78 (1H, dd, J 9.26, 2.1 Hz), 7.36–7.46 (3H, m), 7.53–7.62 (2H, m), 8.00 (1H, t, J 8.0 Hz), 8.03 (1H, s), 8.42 (1H, d, J 7.7 Hz), 8.80 (1H, d, J 8.62 Hz); Anal. Calcd for C$_{21}$H$_{18}$F$_6$N$_2$O.HCl: C, 54.26; H, 4.12; N, 6.02. Found C, 54.04; H, 4.30; N, 5.79.

Example 31

3-(2,8-Bis(Trifluoromethyl)-4-quinolinyl)-3-azetidinol

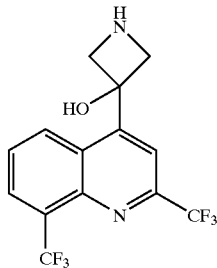

1-Diphenylmethyl-3-(2,8-bis(trifluoromethyl)-4-quinolinyl)-3-azetidinol

To a solution of 4-bromo-2,8-bis(trifluoromethyl)quinoline (500 mg, 1.45 mmol) in dry ether (10 mL) at −78° C. under argon was added n-butyllithium (0.64 mL of 2.5-M, 1.6 mmol). After 20 min a solution of N-diphenylmethyl-3-azetidinone (345 mg, 1.45 mmol) in ether (5 mL) was added dropwise, the mixture stirred for 20 min, water was added and the mixture allowed to warm slowly to room temperature. The mixture was extracted with ether (3×20 mL), the combined extracts dried (MgSO$_4$), concentrated in vacuo and the residue purified by chromatography [SiO$_2$; heptane-EtOAc (3:1)] to give the product (738 mg, 100%) as a pale yellow foam: IR $v_{max}$ (Nujol)/cm$^{-1}$ 3378, 2924, 1456, 1377, 1311, 1145 and 702; NMR $\delta_H$ (400 MHz, CDCl$_3$) 3.74–3.79 (4H, m), 4.45 (1H, s), 7.21–7.37 (6H, m), 7.41–7.46 (4H, m), 7.65–7.69 (2H, m), 8.15 (1H, d, J 7.1 Hz) and 8.35 (1H, d, J 8.6 Hz).

3-(2,8-Bis(Trifluoromethyl)-4-quinolinyl)-3-azetidinol

To a stirred solution of 1-diphenylmethyl-3-(2,8-bis(trifluoromethyl)-4-quinolinyl)-3-azetidinol (690 mg, 1.37 mmol) in dichloroethane (20 mL), at 0° C., was added dropwise 1-chloroethyl chloroformate (0.18 mL, 1.2 eq), the mixture was stirred at 70° C. for 1 h and concentrated in vacuo. The residue was dissolved in MeOH (20 mL), stirred at room temperature for 17 h, concentrated in vacuo and the residue triturated with ether to give the title compound (351 mg, 69%) as a pale-yellow solid: mp 201° C. (dec); NMR $\delta_H$ (400 MHz, CDCl$_3$) 4.44–4.45 (2H, m), 4.76–4.78 (2H, m), 7.95–7.99 (1H, m), 8.23 (1H, s), 8.38–8.42 (2H, m), 9.00 (1H, br s) and 9.47 (1H, br s); Anal. Calcd for C$_{14}$H$_{11}$ClF$_6$N$_2$O: C, 45.12; H, 2.97; N, 7.51. Found: C, 45.21: H, 3.29; N, 7.08.

Example 32

(1'R, 2S)-2-(α-Methoxy-2,8-bis(trifluoromethyl)-4-quinolinemethyl)piperidine Hydrochloride

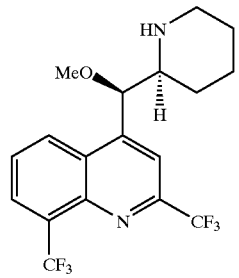

(1'R, 2S)-N-Benzyl-2-(α-methoxy-2,8-bis(trifluoromethyl)-4-quinolinemethyl)piperidine A solution of (1'R, 2'S)-α-(1-benzyl-2-piperidinyl)-2,8-bis(trifluoromethyl)-4-quinolinemethanol (0.73 g, 1.55 mmol) in anhydrous THF (20 mL) was treated with NaH (73 mg, 60% dispersion in oil, 1.82 mmol), stirred for 15 min, treated with iodomethane (0.15 mL, 2.4 mmol), stirred for 1 h, treated carefully with water (2 mL) and concentrated in vacuo. The mixture was treated with water, extracted with CH$_2$Cl$_2$ (2×10 mL), the combined extracts washed with brine, dried (MgSO$_4$), concentrated in vacuo and purified by chromatography [SiO$_2$, EtOAc-heptane (1:3)] to give the product (0.56 g, 74%) as a viscous yellow oil: IR $v_{max}$ (film)/cm$^{-1}$ 2934, 2857, 1601, 1584, 1451, 1430, 1315, 1193, 1142, 771, 740, 700, and 673; NMR $\delta_H$ (400 MHz, CDCl$_3$), 1.2–1.4 (2H, m), 1.45–1.65 (2H, m), 1.7–1.9 (2H, m), 2.52 (1H, m), 2.81 (1H, m), 3.12 (1H, m), 3.27 (1H, m), 3.27 (3H, s), 3.62 (1H, d), 4.05 (1H, d), 5.22 (1H, d), 6.9–7.2 (5H, m), 7.52 (1H, t), 7.80 (1H, s), 8.04 (1H, d), and 8.10 (1H, d).

(1'R, 2S)-2-(α-Methoxy-2,8-bis(trifluoromethyl)-4-quinolinemethyl)piperidine Hydrochloride A mixture of (1'R, 2S)-N-benzy-2-(α-methoxy-2,8-bis(trifluoromethyl)-4-quinolinemethyl)piperidine (0.73 g, 1.55 mmol) and 10% Pd-C (0.1 g) in EtOH (50 mL) was hydrogenated using a Parr apparatus for 4 h, filtered to remove the catalyst, concentrated in vacuo and purified by chromatography [SiO$_2$, CHCl$_3$-MeOH-NH$_4$OH (150:10:1)]. The resulting colourless oil was dissolved in ether, treated with HCl (1-M in ether) and filtered to give the title compound (0.2 g, 49%) as a white solid: m.p. 236–238° C.; IR $v_{max}$ (film)/cm$^{-1}$ 3425 (b), 2697, 1585 (w), 1317, 1187, 1136, 1112, 1069, and 670; NMR $\delta_H$ (400 MHz, DMSO-d$_6$) 1.25–1.45 (2H, m), 1.5–1.7 (3H, m), 2.95 (1H, br m), 3.25 (1H, br m), 3.40 (3H, s), 3.48 (1H, br m), 5.75 (1H, s), 7.93 (1H, s), 8.02 (1H, t), 8.42 (1H, d), 8.5 (1H, br s), 8.90 (1H, d) and 10.1 (1H, br s).

Example 33

α-(1-Amino-2-phenylethyl)-2,8-bis(trifluoromethyl)-4-quinolinemethanol

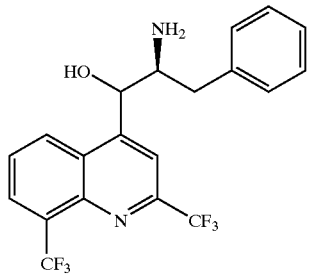

This was prepared by the same method as example 16 using (S)-N(tert-butoxycarbonylphenylalaninal in place of (R)-N-tert-butoxycarbonylprolinal, and the title compound (25 mg, 3%) isolated as a pale solid: IR $v_{max}$ (Nujol)/cm$^{-1}$ 3340, 2925, 1605, 1486, 1377, 1310, 1192, 1181, 1165, 1137,1107 and 1046; NMR $\delta_H$ (400 MHz, CDCl$_3$) 1.42 (2H, br s), 2.72–2.77 (1H, m), 2.94–2.99 (1H, m), 3.06–3.09 (1H, m), 5.37 (1H, s), 6.02 (1H, br m), 7.22–7.35 (5H, m), 7.78 (1H, t, J 8 Hz), 8.06 (1H, d, J 8 Hz), 8.11 (1H, s) and 8.30 (1H, d, J 7 Hz).

Example 34

α-(-Amino-3-methylbutyl)-2,8-bis(trifluoromethyl)-4-quinolinemethanol

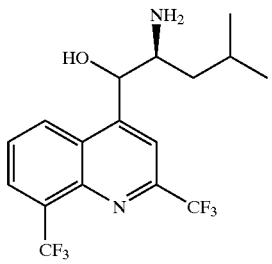

This was prepared by the same method as example 16 using (S)-N-tert-butoxycarbonylleucinal in place of (R)-N-tert-butoxycarbonylprolinal, and the title compound (76 mg, 9%) isolated as a pale solid (4:1 mixture of diastereoisomers): NMR $\delta_H$ (400 MHz, CDCl$_3$) 0.38 (3H, d, J 6.5 Hz), 0.67 (3H, d, J 6.5 Hz), 0.83–0.93 (2H, m), 1.07–1.11 (1H, m), 3.49 (1H, br m), 5.73 and 6.04 (1H, 2×s), 6.78–6.79 and 6.97–6.98 (1H, 2×m), 7.82 (1H, s), 8.01 (1H, t, J 7.5 Hz), 8.22 and 8.18 (1H, 2×s), 8.42 (3H, s), 8.41 and 8.87 (1H, 2×d, J 7.5 Hz).

Example 35

(11S, 2'R)-α-(1-Benzyl-2-piperidinyl)-2,8-bis(trifluoromethyl)-4-quinolinemethanol

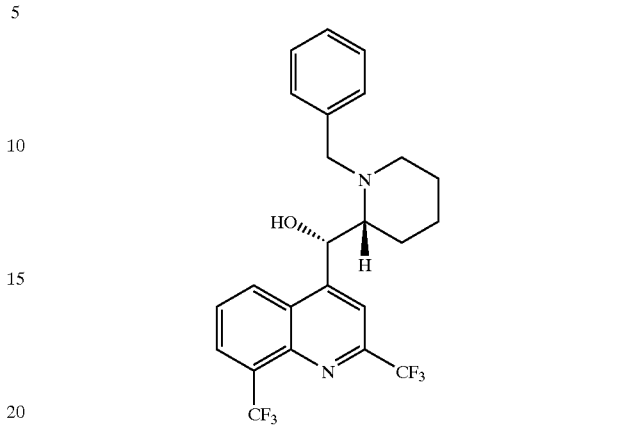

A mixture of (+)-(11S, 2'R)-α-2-piperidinyl-2,8-bis(trifluoromethyl)-4-quinolinemethanol hydrochloride (0.39 g, 0.94 mmol) and K$_2$CO$_3$ (0.39 g, 2.82 mmol) in CH$_2$Cl$_2$ (10 mL) and water (10 mL) was treated with benzyl bromide (0.4 mL, 3.36 mmol), stirred rapidly for 2 h, the phases were separated, the aqueous phase extracted with CH$_2$Cl$_2$ (10 mL), the combined organic phase washed with brine (10 mL), dried (MgSO$_4$), concentrated in vacuo, the resulting yellow oil purified by chromatography [SiO$_2$, heptane-EtOAc (3:1)], dissolved in ether (5 mL), treated with HCl in ether (1 mL) and filtered to give the title compound (180 mg, 41%) as a white solid: mp 221–222° C.; IR $v_{max}$ (Nujol)/cm$^{-1}$ 3404, 2924, 2854, 1601, 1586, 1458, 1308, 1136, 1108, 769 and 663; NMR $\delta_H$ (400 MHz, DMSO-d$_6$) 0.60 (1H, br d, J 18.0 Hz), 1.0 (1H, m), 1.20–1.40 (4H, m), 2.21 (1H, m), 2.90 (1H, m), 3.05 (1H, br d, J 14.0 Hz), 3.42 (1H, d, J 14.0 Hz), 4.58 (1H, d, J 14.0 Hz), 6.02 (1H, m), 7.30-,7.50 (5H, m), 7.71 (1H, t, J 10.0 Hz), 8.10 (1H, d, J 10.0 Hz), 8.19 (1H, d, J 10.0 Hz) and 8.21 (1H, s).

Example 36

(11S, 2'R)-α-(1-Methyl-2-piperidinyl)-2,8-bis(trifluoromethyl)-4-quinolinemethanol

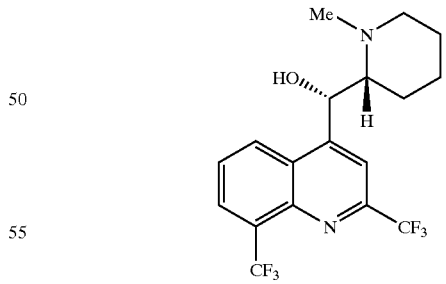

A suspension of (+)-(11S, 2'R)-α-2-piperidinyl-2,8-bis(trifluoromethyl)-4-quinolinemethanol hydrochloride (0.30 g, 0.72 mmol) in 1,2-dichloroethane (10 mL) was treated with 37% aqueous formaldehyde (1 drop), acetic anhydride (0.6 mL, 5.4 mmol) and sodium triacetoxyborohydride (0.3 g, 1.4 mmol), stirred for 3 h, treated with water (10 mL), extracted with CH$_2$Cl$_2$ (2×5 mL) and the combined organic phase washed with NaHCO$_3$ solution (10 mL), dried (MgSO$_4$) and concentrated in vacuo to give the intermediate O-acetylated derivative. The crude product was dissolved in MeOH (5 mL), treated with LiOH (50 mg, 2.1 mmol), stirred for 1 h, concentrated in vacuo to remove the MeOH, diluted with water (1 mL), extracted with CH$_2$Cl$_2$ (2×1 mL), the organic phase dried (MgSO$_4$), concentrated in vacuo and purified by chromatography [SiO$_2$, EtOAc—MeOH (9:1)] to give the free base as a white solid. The solid was dissolved in ether (5 mL), treated with HCl in ether (1 mL) and filtered to give the title compound (152 mg, 53%) as a white solid: mp 209–212° C.; IR $\nu_{max}$ (Nujol)/cm$^{-1}$ 3226, 2925, 1603, 1585, 1459,1376, 1312, 1192, 1136, 1108, 1056, 986, 773 and 668; NMR $\delta_H$ (400 MHz, DMSO-d$_6$) 0.98 (1H, br d, J 18.0 Hz), 1.10–1.30 (1H, m), 1.60–1.80 (4H, m), 3.20–3.25 (4H, m), 3.70 (1H, m), 6.20 (1H, br s), 8.01 (1H, t, J 6.0 Hz), 8.15 (1H, s), 8.42 (1H, d, J 9.0 Hz), 8.62 (1H, d, J 9.0 Hz) and 9.32 (1H, br s).

Example 37

(11S, 2'R)-α-(1-Isobutyl-2-piperidinyl)-2,8-bis(trifluoromethyl)-4-quinolinemethanol

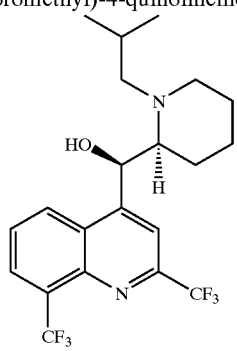

This was prepared from (+)-(11S, 2'R)-α-2-piperidinyl-2,8-bis(trifluoromethyl)-4-quinolinemethanol hydrochloride by the method of example 36 using isobutyraldehyde in place of formaldehyde and the title compound (146 mg, 28%) isolated as a white solid: NMR $\delta_H$ (400 MHz, DMSO-d$_6$) 0.40 (1H, m), 1.18 (3H, d, J 7.0 Hz), 1.25 (3H, d, J 7.0 Hz), 1.00–1.60 (7H, m), 1.90–2.10 (2H, m), 2.80 (1H, m), 3.05 (1H, br d, J 18.0 Hz), 3.85 (1H, s), 5.85 (1H, d, J 8.0 Hz), 7.70 (1H, t, J 10.0 Hz), 8.11 (1H, d, J 9.0 Hz), 8.22 (1H, d, J 9.0 Hz) and 8.30 (1H, s).

Example 38

(11S, 2'R)-α-(1-Phenethyl-2-piperidinyl)-2,8-bis(trifluoromethyl)-4-quinolinemethanol

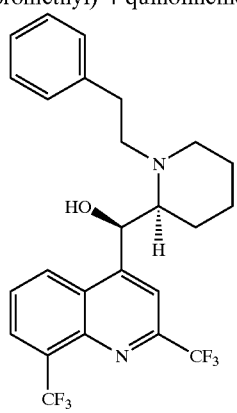

This was prepared from (+)-(11S, 2'R)-α-2-piperidinyl-2,8-bis(trifluoromethyl)-4-quinolinemethanol hydrochloride by the method of example 36 using phenylacetaldehyde in place of formaldehyde and the title compound (31 mg, 9%) isolated as a white solid: NMR $\delta_H$ (400 MHz, DMSO-d$_6$) 0.35 (1H, m), 1.20–1.70 (6H, m), 2.10 (1H, m), 2.82 (1H, m), 3.05–3.30 (3H, m), 4.25 (1H, m), 5.89 (1H, d, J 8.0 Hz), 7.20–7.50 (5H, m), 7.68 (1H, t, J 9.0 Hz), 8.05 (1H, s) and 8.10–8.20 (2H, m).

Example 39

(11S*, 2'R*)-α-(2-Piperidinyl)-2-trifluoromethyl-4-quinolinemethanol (Racemic)

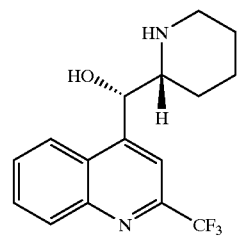

This was prepared as the racemate as reported in Pinder R. M. et al., Antimalarials.II. α-(2-Piperidyl)- and α-(2-pyridyl)-2-trifluoromethyl4-quinolinemethanols. *J. Med. Chem.*, 1968, 11, 267–269

Example 40

(11S, 1'S, 2'S)-α-(1-Amino-2-methyl-1-butyl)-2,8-bis(trifluoromethyl)-4-quinolinemethanol Hydrochloride

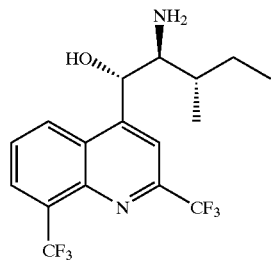

(1S, 2S)-1-(N-tert-Butoxycarbonylamino)-2-methyl-1-butyl 2,8-bis(Trifluoromethyl)quinolin-4-yl Methanone This was prepared from 4-bromo-2,8-bis(trifluoromethyl) quinoline by the method of example 31 using (S)-N-tert-butoxycarbonylleucine-N-carboxy anhydride in place of N-diphenylmethyl-3-azetidinone and the product (247 mg, 26%) isolated as a cream foam: IR $\nu_{max}$ (Nujol)/cm$^{-1}$ 3364, 2924, 2054, 1711, 1682, 1511, 1459, 1433, 1374, 1316, 1200, 1161, 1128, 1107 and 778; NMR $\delta_H$ (400 MHz, CDCl$_3$) 0.82 (3H, t, J 7.3 Hz), 0.99 (3H, d, J 6.4 Hz), 1.04–1.16 (1H, m), 1.36–1.41 (1H, m), 1.45 (9H, s), 1.81–1.86 (1H, m), 5.09 (1H, dd, J 8.9, 4.6 Hz), 5.23 (1H, d, J 8.6 Hz), 7.82 (1H, t, J 8.0 Hz), 8.15 (1H, s), 8.24 (1H, d, J 7.2 Hz) and 8.46 (1H, d, J 9.1 Hz).

(11S, 1'S, 2'S)-α-(1-(N-tert-Butoxycarbonylamino)-2-methyl-1-butyl)-2,8-bis(trifluoromethyl)-4-quinolinemethanol This was prepared from (1S, 2S)-1-(N-tert-butoxycarbonylamino)-2-methyl-1-butyl 2,8-bis(trifluoromethyl) quinolin-4-yl methanone by the method of example 44 and the product (191 mg, 100%) isolated as a colourless oil: IR $\nu_{max}$ (Nujol)/cm$^{-1}$ 3400–3500, 2972, 2936, 2880, 1694, 1603, 1585, 1504, 1310, 1189, 1154, 1112, 910 and 735; NMR $\delta_H$ (400 MHz, CDCl$_3$) 0.81–0.92 (6H, m), 0.96–1.06 (1H, m), 1.31 (9H, s), 1.51–1.53 (1H, m), 1.69 (1H, s), 1.77–1.81 (1H, m), 3.23–3.36 (1H, s), 3.97–4.01 (1H, m), 4.73 (1H, d, J 9.6 Hz), 5.64 (1H, s), 7.73 (1H, t, J 8.0 Hz), 8.05 (1H, s), 8.14 (1H, d, J 7.0 Hz) and 8.47 (1H, d, J 8.5 Hz).

(11S, 2'S, 3'S)-α-(1-Amino-2-methyl-1-butyl)-2,8-bis(trifluoromethyl)-4-quinolinemethanol Hydrochloride This was prepared from (11S, 1'S, 2'S)-α-(1-(N-tert-butoxycarbonylamino)-2-methyl-1-butyl)-2,8-bis(trifluoromethyl)-4-quinolinemethanol by the method of example 42 and the title compound (74 mg, 46%) isolated as a white solid: IR $\nu_{max}$ (Nujol)/cm$^{-1}$ 3200–3600, 2923, 1606, 1588, 1504, 1464, 1378, 1315, 1198, 1144 and 1107; NMR $\delta_H$ (400 MHz, CDCl$_3$) 0.81–0.89 (6H, m), 1.02–1.12 (1H, m), 1.68–1.72 (1H, m), 1.78–1.83 (1H, m), 3.52 (1H, s), 5.87 (1H, t, J 5.0 Hz), 6.79 (1H, d, J 4.5 Hz) 8.00 (1H, t, J 8.1 Hz), 8.23 (1H, s), 8.26 (2H, s), 8.42 (1H, d, J 6.8 Hz) and 8.90 (1H, d, J 8.6 Hz); Anal. Calcd for $C_{17}H_{18}F_6N_2O\cdot HCl\cdot 0.8H_2O$: C, 47.35; H, 4.82; N, 6.50. Found: C, 47.30: H, 4.68; N, 6.32.

Example 41

α-(2-Amino-2-propyl)-2,8-bis(trifluoromethyl)-4-quinolinemethanol

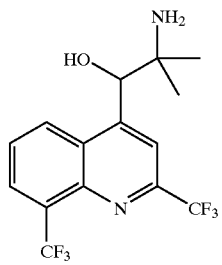

α-(2-Nitro-2-propyl)-2,8-bis(trifluoromethyl)-4-quinolinemethanol

A mixture of 2,8-bis(trifluoromethyl)-4-quinolinecarboxaldehyde (200 mg, 0.85 mmol), 2-nitropropane (0.1 mL, 1.1 mmol) and Amberlyst 21 resin (200 mg) was stirred at room temperature for 17 h, treated with CH$_2$Cl$_2$ (3 mL), filtered to remove the resin, the filtrate concentrated in vacuo to give a viscous oil which was crystallised from heptane to give a white solid which was recrystallised (ether/heptane) to give the product (140 mg, 51%) as a white crystalline solid: IR $\nu_{max}$ (Nujol)/cm$^{-1}$ 3484, 2923, 1544, 1311, 1134 and 780; NMR $\delta_H$ (400 MHz, CDCl$_3$) 1.37 (3H, s), 1.54 (3H, s), 3.03 (1H, d, J 4.5 Hz), 6.36 (1H, d, J 4.4 Hz), 7.80 (1H, t, J 8.1 Hz), 8.07 (1H, s), 8.21 (1H, d, J 7.1 Hz) and 8.44 (1H, d, J 8.5 Hz).

α-(2-Amino-2-propyl)-2,8-bis(trifluoromethyl)-4-quinolinemethanol

A solution of α-(2-nitro-2-propyl)-2,8-bis(trifluoromethyl)-4-quinolinemethanol (200 mg, 0.52 mmol) in acetic acid (2 mL) was treated slowly with zinc dust, stirred at room temperature for 30 min, filtered through Celite, concentrated in vacuo and the resulting viscous oil purified by chromatography [SiO$_2$, EtOAc] to give the title compound (63 mg, 31%) as a white solid: mp 175–176° C.; IR $\nu_{max}$ (Nujol)/cm$^{-1}$ 3372, 2925, 1741, 1310,1145, 1111, 756 and 684; NMR $\delta_H$ (400 MHz, CDC$_3$) 0.84 (3H, s), 0.99 (3H, s), 3.37 (1H, br s), 5.69 (1H, d, J 3.9 Hz), 6.01 (1H, d, J 4.0 Hz), 7.92 (1H, t, J 8.7 Hz), 8.35 (1H, d, J 7.5 Hz) and 8.75 (1H, d, J 8.6 Hz); Anal. Calcd for $C_{14}H_{11}ClF_6N_2O$: C, 45.12; H, 2.97; N, 7.51. Found: C, 45.21: H, 3.29; N, 7.08.

Example 42

(11R, 2'S)-α-(2-pyrrolidinyl)-2,8-bis(trifuoromethyl)-4-quinolinemethanol Hydrochloride

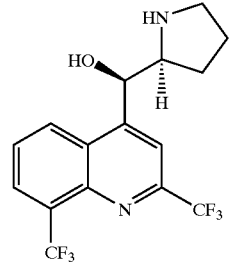

A solution of (11R, 2'S)-α-(1-tert-butoxycarbonyl-2-pyrrolidinyl)-2,8-bis(trifluoromethyl)-4-quinolinemethanol (600 mg, 1.29 mmol) in dioxane (2 mL) was treated with 4-M HCl in dioxane (2 mL), stirred at room temperature for 2 h, concentrated in vacuo and the resulting solid triturated with ether and filtered ti give the title compound (406 mg, 79%) as a white solid: mp 230° C. (dec); IR $\nu_{max}$ (Nujol)/cm$^{-1}$ 3229, 2923, 2854, 2775, 1458, 1434, 1376, 1313, 1192, 1134, 1110 and 776; NMR $\delta_H$ (400 MHz, CDCl$_3$) 1.46–1.60 (1H, m), 1.74–1.83 (1H, m), 1.87–2.00 (2H, m), 3.15–3.28 (2H, m), 3.89–3.94 (1H, m), 6.03 (1H, s), 6.82 (1H, d, J 4.1 Hz), 8.01 (1H, t, J 7.7 Hz), 8.18 (1H, s), 8.43 (1H, d, J 7.2 Hz) and 8.86 (1H, d, J 8.6 Hz); Anal. Calcd for $C_{16}H_{14}F_6N_2O\cdot HCl$: C, 47.95; H, 3.77; N, 6.99. Found: C, 47.74: H, 3.76; N, 6.99.

Example 43

(11R, 2'S)-α-(1-tert-Butoxycarbonyl-2-pyrrolidinyl)-2,8-bis(trifluoromethyl)-4-quinolinemethanol

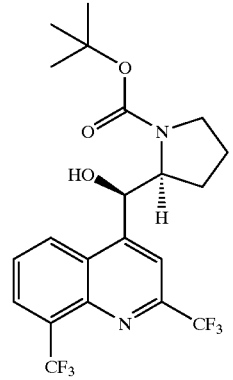

(2S)-(1-tert-Butoxycarbonyl-2-pyrrolidinyl)2,8-bis(trifluoromethyl)quinolin-4-yl Methanone This was prepared from 4-bromo-2,8-bis(trifluoromethyl) quinoline by the method of example 31 using (S)-N-tert-butoxycarbonylproline methyl ester in place of N-diphenylmethyl-3-azetidinone and the product (1.32 g, 29%) isolated as a cream solid: IR $\nu_{max}$ (Nujol)/cm$^{-1}$ 2979, 2883, 1748, 1698, 1401, 1368, 1312, 1160 and 1110; NMR $\delta_H$ (400 CDCl$_3$) (mixture of 2 rotamers) 1.41 and 1.45 (9H, 2×s), 1.79–2.13 (3H, m), 2.11–2.31 (1H, m), 3.32–3.70 (2H, m), 5.09 and 5.16 (1H, 2×dd, J 8.8, 4.3 and J 9.0, 5.5 Hz), 7.78–7.83 (1H, m), 8.03 and 8.04 (1H, 2×s), 8.18–8.29 (1H, m), 8.41 and 8.51 (1H, 2×d, J 8.5 and J 8.5 Hz).

(11R, 2'S)-α-(1-tert-Butoxycarbonyl-2-pyrrolidinyl)-2,8-bis(trifluoromethyl)-4-quinolinemethanol A solution of (2S)-(1-tert-butoxycarbonyl-2-pyrrolidinyl) 2,8-bis(trifluoromethyl)quinolin-4-yl methanone (1.0 g, 2.16 mmol) in THF (20 mL) at −70° C. was treated with 1M-DIBAL in toluene (10.8 mL, 10.8 mmol), stirred at −70° C. for 7 h, treated with MeOH (1 mL) and water (1 mL), stirred at room temperature overnight, diluted with EtOAc (10 mL), dried (MgSO$_4$) and concentrated in vacuo. The crude product was purified by chromatography [SiO$_2$, heptane-EtOAc (2:1)] and the resulting solid was triturated with heptane and filtered to give the title compound (712 mg, 71%) as a cream solid: mp 166.8–167.3° C.; IR ν$_{max}$ (Nujol)/cm$^{-1}$ 3415, 2924, 2854, 1651, 1604, 1586, 1459, 1432, 1418, 1371, 1309, 1189, 1162, 1134 and 1109; NMR δ$_H$ (400 MHz, CDCl$_3$) 1.45–1.48 (1H, m), 1.57 (9H, s), 1.63–1.64 (1H, m), 1.82–1.90 (2H, m), 3.27–3.40 (1H, s), 3.41–3.56 (1H, s), 4.19–4.22 (1H, m), 6.16 (1H, s), 7.69 (1H, t, J 7.7 Hz), 8.10–8.12 (2H, m) and 8.63 (1H, s).

Example 44

(11S, 2'S)-α-(1-tert-Butoxycarbonyl-2-pyrrolidinyl)-2,8-bis(trifluoromethyl)-4-quinolinemethanol

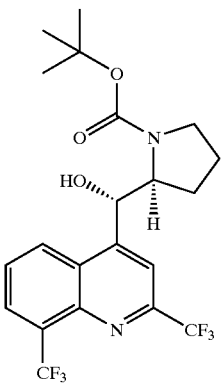

A solution of (2S)-(1-tert-butoxycarbonyl-2-pyrrolidinyl) 2,8-bis(trifluoromethyl)quinolin-4-yl methanone (493 mg, 1.07 mmol) in THF (10 mL) at −70° C. was treated with K-selectride (1-M in THF) (2.14 mL, 2.14 mmol), stirred at −70° C. for 7 h, warmed to room temperature overnight, cooled to 0° C., treated with 35% H$_2$O$_2$ solution (0.5 mL), stirred at room temperature for 3 h, treated with NH$_4$Cl solution (1 mL) and Na$_2$SO$_4$ solution (1 mL), dried (MgSO$_4$) and concentrated in vacuo. The crude product was purified by chromatography [SiO$_2$, heptane-EtOAc (3:1)], the resulting solid triturated with heptane and filtered to give the title compound (240 mg, 48%) as a white solid: mp 195.5–196.6° C. (dec) IR ν$_{max}$ (Nujol)/cm$^{-1}$ 3500–3200, 2924, 2854, 1668, 1597, 1585, 1460, 1431, 1410, 1370, 1306, 1162, 1143, 1112, 1098 and 771; NMR δ$_H$ (400 MHz, CDCl$_3$) 1.26–1.39 (1H, m), 1.52 (10H, s), 1.71–1.78 (2H, m), 3.34–3.38 (1H, m), 3.46–3.59 (1H, m), 4.36–4.42 (1H, m), 5.33 (1H, d, J 8.4 Hz), 6.38–6.75 (1H, s), 7.71 (1H, t, J 8.1 Hz), 7.93 (1H, s), 8.16 (1H, d, J 6.9 Hz) and 8.58 (1H, d, J 8.0 Hz).

Example 45

(11S, 2'S)-α-(2-Pyrrolidinyl)-2,8-bis(trifluoromethyl)-4-quinolinemethanol Hydrochloride

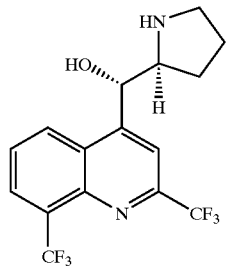

This was prepared from (11S, 2'S)-α-(1-tert-butoxycarbonyl-2-pyrrolidinyl)-2,8-bis(trifluoromethyl)-4-quinolinemethanol by the method of example 42 and the title compound (148 mg, 95%) isolated as a white solid: mp 246° C. (dec); IR ν$_{max}$ (Nujol)/cm$^{-1}$ 3200–3300, 2924, 2854, 1605, 1586, 1461, 1435, 1399, 1375, 1311, 1297, 1190, 1159, 1143, 1111, 1099 and 780; NMR δ$_H$ (400 MHz, CDCl$_3$) 1.87–2.02 (4H, m), 3.06–3.10 (1H, m), 3.22–3.27 (1H, m), 3.81–3.86 (1H, m), 5.92 (1H, d, J 5.1 Hz), 7.01–7.14 (1H, s), 8.01 (1H, t, J 7.7 Hz), 8.29 (1H, s), 8.43 (1H, d, J 6.9 Hz), 8.78 (1H, d, J 8.0 Hz) and 8.82–9.26 (1H, br s); Anal. Calcd for C$_{16}$H$_{14}$F$_6$N$_2$O.HCl: C, 47.95; H, 3.77; N, 6.99. Found: C, 47.89: H, 3.74; N, 7.03.

Example 46

(11R*, 2'S*)-2-Hydroxy-8-methyla-(α2-piperidinyl)-4-quinolinemethanol (Racemic)

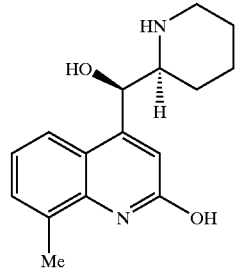

2-Hydroxy-8-methyl-α-(2-pyridyl)-4-quinolinemethanol

This was prepared from 4-bromo-2-hydroxy-8-methylquinoline by the method of example 31 using 2-pyridinecarboxaldehyde in place of N-diphenylmethyl-3-azetidinone and the product (300 mg, 43%) isolated as a cream solid: mp 215° C. (dec); IR ν$_{max}$ (Nujol)/cm$^{-1}$ 2924, 2854, 1651, 1599, 1573, 1466, 1379, 1062, 780, 754 and 744; NMR δ$_H$ (400 MHz, DMSO-d$_6$) 3.19 (1H, d, J 5.1 Hz), 3.34 (3H, s), 6.11 (1H, d, J 4.6 Hz), 6.41 (1H, d, J 4.7 Hz), 6.76 (1H, s), 6.99 (1H, t, J 7.8 Hz), 7.26–7.29 (2H, m), 7.58 (1H, d, J 8.0 Hz), 7.70 (1H, d, J 8.0 Hz), 7.81 (1H, dt, J 7.6, 1.8 Hz), 8.49 (1H, d, J 5.6 Hz) and 10.80 (1H, s); Anal. Calcd for C$_{16}$H$_{14}$N$_2$.0.15 H$_2$O: C, 71.44; H, 5.36; N, 10.41. Found: C, 71.62; H, 5.30; N, 10.38; M/Z 267 (M+H)$^+$.

(11R*, 2'S*)-2-Hydroxy-8-methyl-α-(2-piperidinyl)-4-quinolinemethanol

A solution of 2-hydroxy-8-methyl-α-(2-pyridyl)-4-quinolinemethanol (100 mg, 0.38 mmol) in EtOH (10 mL) and acetic acid (5 mL) was treated with 5% Pt/C (5 mg), hydrogenated for 16 h, filtered and concentrated in vacuo. The crude product was treated with $Na_2CO_3$ solution (5 mL), extracted with EtOAc (2×5 mL), the combined organic phase was dried ($MgSO_4$), concentrated in vacuo and the resulting solid triturated with ether and filtered to give the title compound (95 mg, 92%) as a cream solid: mp 225° C. (dec); IR $v_{max}$ (Nujol)/cm$^{-1}$ 3176, 2925, 2854, 1654, 1607, 1464, 1377, 875 and 749; NMR $\delta_H$ (400 MHz, DMSO-$d_6$) 1.17–1.26 (3H, m), 1.41–1.46 (2H, m), 1.71–1.74 (1H, m), 2.44 (3H, s), 2.71–2.73 (1H, m), 2.94–2.97 (1H, m), 4.90 (1H, t, J 4.0 Hz), 5.41 (1H, d, J 2.5 Hz), 6.57 (1H, s), 7.11 (1H, t, J 7.7 Hz), 7.35 (1H, d, J 6.8 Hz) and 7.70 (1H, d, J 8.1 Hz); Anal. Calcd for $C_{16}H_{20}N_2O_2.0.15\ H_2O$: C, 69.87; H, 7.44; N, 10.18. Found: C, 69.78: H, 7.38; N, 10.02.

Example 47

(11R*, 2'S*)-2-Amino-α-(2-piperidinyl)-4-quinolinemethanol (Racemic)

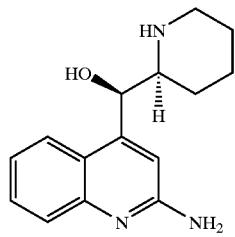

2-Amino-8-α-(2-pyridyl)-4-quinolinemethanol

This was prepared from 4-bromo-2-aminoquinoline by the method of example 31 using 2-pyridinecarboxaldehyde in place of N-diphenylmethyl-3-azetidinone and the product (376 mg, 26%) isolated as a cream solid,: mp 159° C. (dec); IR $v_{max}$ (Nujol)/cm$^{-1}$ 3426, 3304, 3126, 2924, 2854, 1645, 1618, 1595, 1568, 1466, 1430, 1077 and 752; NMR $\delta_H$ (400 MHz, CDCl$_3$) 6.22 (1H, d, J 4.6 Hz), 6.33 (1H, d, J 4.6 Hz), 6.44 (2H, s), 7.03 (1H, s), 7.06 (1H, t, J 7.6 Hz), 7.26 (1H, t, J 6.8 Hz), 7.35–7.45 (2H, m), 7.54 (1H, d, J 8.0 Hz), 7.77–7.82 (1H, m), 7.91 (1H, d, J 7.5 Hz), 8.47 (1H, dd, J 5.0, 1.0 Hz); Anal. Calcd for $C_{15}H_{13}N_3O.0.25\ H_2O$: C, 70.43; H, 5.32; N, 16.43. Found: C, 70.50; H, 5.29; N, 16.11.

(11R*, 2'S*)-2-Amino-α-(2-piperidinyl)-4-quinolinemethanol

This was prepared from 2-amino-α-(2-pyridyl)-4-quinolinemethanol by the method of example 46 and the title compound (97 mg, 41%) isolated as a cream solid: mp 225° C. (dec); IR $v_{max}$ (Nujol)/cm$^{-1}$ 3400–3100, 2927, 2854, 1677, 1458, 1403, 1377 and 1117; NMR $\delta_H$ (400 MHz, CDCl$_3$) 1.29–1.36 (3H, m), 1.60–1.80 (5H, m), 3.04 (1H, m), 3.33 (1H, m), 5.91 (1H, s), 6.83 (1H, m), 7.37 (1H, m), 7.60 (1H, m), 7.84 (2H, m), 8.47 (1H, m) and 10.48 (1H, m); Anal. Calcd for $C_{15}H_{19}N_3O.2.5\ HCl.0.75\ H_2O$: C, 49.77; H, 6.40; N, 11.61. Found: C, 49.72: H, 6.33; N, 11.33.

Example 48

(11R*, 2'S*)-2-Methoxy-8-methyl-α-(2-piperidinyl)-4-quinolinemethanol (Racemic)

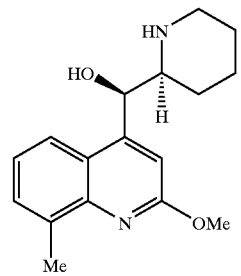

2-Methoxy-8-methyl-α-(2-pyridyl)-4-quinolinemethanol

This was prepared from 4-bromo-2-methoxy-8-methylquinoline by the method of example 31 using 2-pyridinecarboxaldehyde in place of N-diphenylmethyl-3-azetidinone and the product (848 mg, 64%) isolated as a cream solid: mp 126.8–127.6° C.; IR $v_{max}$ (Nujol)/cm$^{-1}$ 3200–3000, 2924, 2854, 1615, 1598, 1585, 1478, 1343 and 754; NMR $\delta_H$ (400 MHz, CDCl$_3$) 2.69 (3H, s), 4.05 (3H, s), 5.16–5.43 (1H 6.33 (1H, s), 6.96 (1H, s), 7.08 (1H, d, J 8.1 Hz), 7.18–7.27 (2H, m), 7.46 (1H, d, J 7.1 Hz), 7.53–7.57 (1H, m), 7.83 (1H, d, J 8.7 Hz) and 8.62 (1H, d, J 5.1 Hz); Anal. Calcd for $C_{17}H_{16}N_2O_2.0.1H_2O$: C, 72.37; H, 5.79; N, 9.93. Found: C, 72.21; H, 5.71; N, 9.86.

(11R*, 2'S*)-2-Methoxy-8-methyl-α-(2-piperidinyl)-4-quinolinemethanol

This was prepared from 2-methoxy-8-methyl-α-(2-pyridyl)-4-quinolinemethanol by the method of example 46 and the title compound (72 mg, 25%) isolated as a white solid: IR $v_{max}$ (Nujol)/cm$^{-1}$ 3287, 2924, 2854, 1606, 1582, 1460, 1440, 1381, 1336, 1231, 1128, 1038, 878 and 765; NMR $\delta_H$ (400 MHz, CDCl$_3$) 1.10–1.36 (4H, m), 1.52–1.71 (2H, m), 2.67–2.74 (1H, m), 2.71 (3H, s), 3.03–3.14 (2H, m), 4.07 (3H, s), 5.34 (1H, m), 7.14 (1H, s), 7.26 (1H, m), 7.47 (1H, m), and 7.66 (1H, m); Anal. Calcd for $C_{17}H_{22}N_2O_2.0.1H_2O$: C, 70.85; H, 7.77; N, 9.72. Found: C, 70.84: H, 7.67; N, 9.64.

Adenosine Receiptor Binding

Binding Affinities at hA$_{2A}$ Receptors

The compounds were examined in an assay measuring in vitro binding to human adenosine A$_{2A}$ receptors by determining the displacement of the adenosine A$_{2A}$ receptor selective radioligand [$^3$H]-CGS 21680 using standard techniques. The results are summarised in Table 1.

TABLE 1

| Compound | K$_i$ (nM) |
| --- | --- |
| Example 2 | 41 |
| Example 3 | 2530 |
| Example 4 | 24 |
| Example 5 | 1740 |
| Example 7 | 45 |
| Example 8 | 419 |
| Example 9 | 182 |
| Example 11 | 63 |
| Example 13 | 192 |
| Example 14 | 1780 |
| Example 15 | 1172 |

TABLE 1-continued

| Compound | $K_i$ (nM) |
| --- | --- |
| Example 22 | 1500 |
| Example 23 | 2730 |
| Example 24 | 2450 |
| Example 25 | 1270 |
| Example 26 | 2804 |
| Example 32 | 226 |
| Example 34 | 1215 |
| Example 38 | 906 |
| Example 39 | 404 |
| Example 40 | 609 |
| Example 42 | 462 |
| Example 43 | 2716 |
| Example 45 | 2056 |
| Example 48 | 1105 |

Evaluation of Potential Anti-Parkinsonian Activity in vivo

Haloperidol-induced Bypolocomotion Model

It has previously been demonstrated that adenosine antagonists, such as theophylline, can reverse the behavioural depressant effects of dopamine antagonists, such as haloperidol, in rodents (Mandhane et al., *Eur. J. Pharmacol.* 1997, 328, 135–141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25–30 g) obtained from TUCK, UK, are used for all experiments. Animals are housed in groups of 8 [cage size—40 (width)×40 (length)×20 (height)cm] under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Liquid injectable haloperidol (1 ml Serenance ampoules from Baker Norton, Harlow, Essex, each containing haloperidol BP 5 mg, batch #P424) are diluted to a final concentration of 0.02 mg/ml using saline. Novel test compounds are typically prepared as aqueous suspensions in 8% Tween. All compounds are administered intraperitoneally in a volume of 10 ml/kg.

Procedure 1.5 hours before testing, mice are administered 0.2 mg/kg haloperidol, a dose that reduces baseline locomotor activity by at least 50%. Test substances are typically administered 5–60 minutes prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 3×6 array of photocells linked to a computer, which tabulates beam breaks. Mice are left undisturbed to explore for 1 hour, and the number of beams breaks made during this period serves as a record of locomotor activity which is compared with data for control animals for statistically significant differences. In this model, Example 39, administered intraperitoneally at a dose of 10 mg/kg, significantly reversed haloperidol-induced hypolocomotion.

6-OHDA Model

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal doparnine is lost (ca 80–85%) before symptoms are observed. The loss of striatal dopamine results in abnormal activity of the basal ganglia, a series of nuclei which regulate smooth and well co-ordinated movement (Blandini et al., 1996 *Mol. Neurobiol.* 1996, 12, 73–94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersenstive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parldnson's Disease.

Animals

Male Sprague-Dawley rats, obtained from Charles River, were used for all experiments. Animals were housed in groups of 5 under 12 hr light/dark cycle (lights on 08:00 hr), in a temperature (20±2° C.) and humidity (55±15%) controlled environment. Animals had free access to food and water, and allowed at least 7 days to acclimatize after delivery before experimental use.

Drugs

Ascorbic acid, desipramine, 6-OHDA and apomorphine were obtained from Sigma-Aldrich, Poole, UK. 6-OHDA was freshly prepared as a solution in 0.2% ascorbate at a concentration of 4 mg/mL prior to surgery. Desipramine was dissolved in warm saline, and administered in a volume of 1 ml/kg. Apomorphine was dissolved in 0.02% ascorbate and administered in a volume of 2 mL/kg. Test compounds were suspended in 8% Tween and injected in a volume of 2 mL/kg.

Surgery 15 minutes prior to surgery, animals were given an intraperitoneal injection of the noradrenergic uptake inhibitor desipramine (25 mg/kg) to prevent damage to non-dopamine neurones. Animals were then placed in an anaesthetic chamber and anaesthetised using a mixture of oxygen and isoflurane. Once unconscious, the animals were transferred to a stereotaxic frame, where anaesthesia was maintained through a mask. The top of the animal's head was shaved and sterilised using an iodine solution. Once dry, a 2 cm long incision was made along the midline of the scalp and the skin retracted and clipped back to expose the skull. A small hole was then drilled through the skill above the injection site. In order to lesion the nigrostriatal pathway, the injection cannula was slowly lowered to position above the right medial forebrain bundle at −3.2 mm anterior posterior, −1.5 mm medial lateral from bregma, and to a depth of 7.2 mm below the duramater. 2 minutes after lowing the cannula, 2 μL of 6-OHDA was infused at a rate of 0.5 μL/min over 4 minutes, yeilding a final dose of 8 μg. The cannula was then left in place for a further 5 minutes to facilitate diffusion before being slowly withdrawn. The skin was then sutured shut using Ethicon W501 Mersilk, and the animal removed from the strereotaxic frame and returned to its homecage. The rats were allowed 2 weeks to recover from surgery before behavioural testing.

Apparatus

Rotational behaviour was measured using an eight station rotameter system provided by Med Associates, San Diego, USA. Each station was comprised of a stainless steel bowl (45 cm diameter×15 cm high) enclosed in a transparent Plexiglas cover running around the edge of the bowl, and extending to a height of 29 cm. To assess rotation, rats were placed in cloth jacket attached to a spring tether connected to optical rotameter positioned above the bowl, which assessed movement to the left or right either as partial (45°) or full (360°) rotations. All eight stations were interfaced to a computer that tabulated data Procedure To reduce stress during drug testing, rats were initially habituated to the apparatus for 15 minutes on four consecutive days. One the test day, rats were given an intraperitoneal injection of test compound 30 minutes prior to testing. Immediately prior to testing, animals were given a subcutaneous injection of a subthreshold dose of apomorphine, then placed in the harness and the number of rotations recorded for one hour. The total number of full contralatral rotations during the hour test period served as an index of antiparkinsonian drug efficacy.

What is claimed is:

1. A method of treating a disorder in which the blocking of adenosine $A_{2A}$ receptor is beneficial, comprising administering to a subject in need of such treatment an effective dose of a compound of formula I:

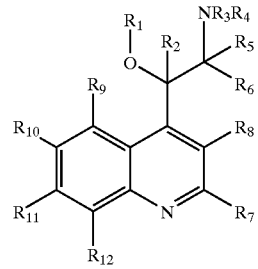

(I)

wherein:

$R_1$ is hydrogen or alkyl;

$R_2$ is selected from the group consisting of hydrogen, alkyl, aryl and 4, 5, 6, 7 or 8 membered saturated or partially unsaturated heterocyclic rings containing one or more heteroatoms selected from O, S and N;

$R_3$ and $R_4$ are independently selected from the group consisting of hydrogen, alkyl, aryl, $COR_{13}$, $CO_2R_{13}$, $CONR_{13}R_{14}$, $CONR_{13}NR_{14}R_{15}$, $SO_2R_{13}$, $SO_2NR_{13}R_{14}$, $SO_2NR_{13}NR_{14}R_{15}$ and 4, 5, 6, 7 or 8 membered saturated or partially unsaturated heterocyclic rings containing one or more heteroatoms selected from O, S and N, or together may form a 3, 4, 5, 6, 7 or 8 membered saturated, partially unsaturated or aromatic heterocyclic ring optionally containing one or more additional heteroatoms selected from the group consisting of O, S and N;

or $R_1$ and $R_4$ together may form a 5, 6 or 7 membered saturated or partially unsaturated heterocyclic ring optionally containing an additional heteroatom selected from the group consisting of O, S and N;

or $R_2$ and $R_3$ together may form a 4, 5, 6 or 7 membered saturated or partially unsaturated heterocyclic ring optionally containing one or more additional heteroatoms selected from the group consisting of O, S and N;

$R_5$ and $R_6$ are independently selected from the group consisting of hydrogen, alkyl, aryl and 4, 5, 6, 7 or 8 membered saturated or partially unsaturated heterocyclic rings containing one or more heteroatoms selected from the group consisting of O, S and N, or together may form a 3, 4, 5, 6 or 7 membered saturated or partially unsaturated carbocyclic ring or a 4, 5, 6, 7 or 8 membered saturated or partially unsaturated heterocyclic ring containing one or more heteroatoms selected from the group consisting of O, S and N; or $R_3$ and $R_5$ together may form a 4, 5, 6 or 7 membered unbridged, saturated or partially unsaturated heterocyclic ring optionally containing one or more additional heteroatoms selected from the group consisting of O, S and N;

wherein said carbocyclic or said heterocyclic ring when partially unsaturated or aromatic may be fused to an aryl ring;

and wherein said disorder is selected from the group consisting of movement disorders and depression;

with the proviso that where $R_3$ and $R_5$ together form a ring, then $R_3$ and $R_4$ do not also form a ring;

$R_7$, $R_8$, $R_9$, $R_{10}$, $R_{11}$ and $R_{12}$ are independently selected from the group consisting of hydrogen, alkyl, aryl, 4, 5, 6, 7 or 8 membered saturated or partially unsaturated heterocyclic rings containing one or more heteroatoms selected from the group consisting of O, S and N, hydroxy, halogen, nitro, cyano, alkoxy, aryloxy, $COR_{13}$, $OCOR_{13}$, $CO_2R_{13}$, $SR_{13}$, $SOR_{13}$, $SO_2R_{13}$, $SO_2NR_{13}R_{14}$, $CONR_{13}R_{14}$, $CONR_{13}NR_{14}R_{15}$, $OCONR_{13}R_{14}$, $NR_{13}R_{14}$, $NR_{13}COR_{14}$, $NR_{15}CONR_{13}R_{14}$, $NR_{13}CO_2R_{14}$, $NR_{13}SO_2R_{14}$, $CR_{13}NOR_{14}$, $NR_{13}CONR_{14}NR_{15}R_{16}$, $NR_{13}NR_{14}CO_2R_{15}$, $NR_{13}NR_{14}CONR_{15}R_{16}$, $NR_{13}NR_{14}COR_{15}$, $NR_{13}NR_{14}SO_2R_{15}$, $SO_2NR_{13}NR_{14}R_{15}$, $NR_{13}SO_2NR_{14}NR_{15}R_{16}$ and $NR_{13}SO_2NR_{14}R_{15}$, wherein $R_{13}$, $R_{14}$, $R_{15}$ and $R_{16}$ are independently selected from the group consisting of hydrogen, alkyl and aryl, or a pharmaceutically acceptable salt thereof.

2. A method according to claim 1, wherein $R_1$ is hydrogen or methyl.

3. A method according to claim 1, wherein $R_1$ forms a 5 or 6 membered ring with $R_4$.

4. A method according to claim 1, wherein $R_2$ is hydrogen.

5. A method according to claim 1 wherein $R_2$ forms a 4, 5 or 6 membered ring with $R_3$.

6. A method according to claim 1, wherein $R_3$ is hydrogen, methyl, acetyl, phenyl, benzyl, cyclobutyl or isobutyl.

7. A method according to claim 1, wherein $R_3$ forms a 5 or 6 membered ring with $R_4$.

8. A method according to claim 1, wherein $R_3$ forms a 5 or 6 membered ring with $R_5$.

9. A method according to claim 1, wherein $R_4$ is hydrogen, methyl, acetyl, phenyl, benzyl, phenylethyl, cyclobutyl or isobutyl.

10. A method according to claim 1, wherein $R_5$ is hydrogen, benzyl, isobutyl or secondary butyl.

11. A method according to claim 1, wherein $R_6$ is hydrogen, benzyl, isobutyl or secondary butyl.

12. A method according to claim 1, wherein at least one of $R_7$ to $R_{12}$ is a substituent group other than hydrogen.

13. A method according to claim 1, wherein one or both of $R_7$ and $R_{12}$ are substituents other than trifluoromethyl.

14. A method according to claim 1, wherein if any of $R_7$ to $R_{12}$ is $NR_{13}COR_{14}$, then $R_{13}$ of the $NR_{13}COR_{14}$ group is hydrogen.

15. A method according to claim 1, wherein $R_8$, $R_9$, $R_{10}$ and/or $R_{11}$ is hydrogen.

16. A method according to claim 1, wherein $R_7$ is selected from the group consisting of hydroxy, alkoxy and $NR_{13}R_{14}$.

17. A method according to claims 1, wherein $R_{12}$ is selected from the group consisting of hydrogen and alkyl.

18. A method according to claim 1, wherein the compounds of formula (I) are selected from compounds in which $R_2$ is H or alkyl and the stereochemical configuration at the carbon atom bound to the 4-position of the quinoline ring is R.

19. A method according to claim 1, wherein the disorder is caused by the hyperfunctioning of adenosine $A_{2A}$ receptors.

20. A method according to claim 1, wherein said disorder is a movement disorder.

21. A method of neuroprotection comprising administration to a subject in need of treatment for a disorder other than Alzheimer's Disease an effective dose of a compound of formula (I) as set out in claim 1 or a pharmaceutically acceptable salt thereof.

22. A method according to claim 20, wherein the movement disorder is Parkinson's disease.

23. A method according to claim 22, for treatment of drug-induced Parkinsonism, post-encephalitic Parkinsonism, Parkinsonism induced by poisoning or post-traumatic Parkinson's disease.

24. A method according to 20, wherein the movement disorder is progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism or spasticity.

25. A method according to claim 20, wherein the compound of formula (I) is administered in combination with one or more additional drugs that are beneficial in the treatment of movement disorders, the components being in the same formulation or in separate formulations for administration simultaneously or sequentially.

26. A method according to claim 25, wherein the movement disorder is Parkinson's disease.

27. A method according to claim 25, wherein at least one of the additional drugs is L-DOPA.

28. A method according to claim 1, wherein said disorder is depression.

29. A method according to claim 21, wherein said method is for neuroprotection in a subject suffering from, or at risk from, a neurodegenerative disorder.

30. A method according to claim 29, wherein said neurodegenerative disorder is a movement disorder.

31. A method according to claim 1, wherein the compounds of formula (I) are selected from (1R,8aS)-1,5,6,7,8,8a-hexahydro-1-(2,8-bis(trifluoromethyl)-4-quinolinyl)-3H-oxazolo[3,4-a]pyridine, (11R,2'S)-α-(1-methyl-2-piperidinyl)-2,8-bis(trifluoromethyl)-4-quinolinemethanol, (−)-(11R, 2'S)-α-2-piperidinyl-2,8-bis(trifluoromethyl)-4-quinolinemethanol, (−)-(11R, 2'R)-α-2-piperidinyl-2,8-bis(trifluoromethyl)-4-quinolinemethanol and (11S*, 2'R*)-α-(2-piperidinyl)-2-trifluoromethyl-4-quinolinemethanol.

32. A method according to claim 30, wherein said movement disorder is Parkinson's disease, progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, or spasticity.

33. A method according to claim 29, wherein the subject is human.

* * * * *